United States Patent [19]

Breault

[11] Patent Number: 5,994,353
[45] Date of Patent: Nov. 30, 1999

[54] AROMATIC COMPOUNDS AND PHARMACEUTICAL COMPOSITIONS CONTAINING THEM

[75] Inventor: Gloria Anne Breault, Macclesfield, United Kingdom

[73] Assignee: Zeneca Limited, United Kingdom

[21] Appl. No.: 08/973,887

[22] PCT Filed: Jun. 17, 1996

[86] PCT No.: PCT/GB96/01442

§ 371 Date: Dec. 16, 1997

§ 102(e) Date: Dec. 16, 1997

[87] PCT Pub. No.: WO97/00863

PCT Pub. Date: Jan. 9, 1997

[30] Foreign Application Priority Data

Jun. 20, 1995 [GB] United Kingdom .................. 9512476
Jan. 25, 1996 [GB] United Kingdom .................. 9601462
Mar. 30, 1996 [GB] United Kingdom .................. 9606831

[51] Int. Cl.$^6$ .......................... A01N 43/58; C07D 401/00
[52] U.S. Cl. .................. 514/247; 514/252; 544/238; 544/240
[58] Field of Search .................. 514/247, 252; 544/238, 240

[56] References Cited

U.S. PATENT DOCUMENTS

| | | | |
|---|---|---|---|
| 3,632,760 | 1/1972 | Shen et al. | 424/230 |
| 3,657,430 | 4/1972 | Shen et al. | 424/230 |
| 4,152,452 | 5/1979 | Douglas et al. | 424/304 |
| 4,206,145 | 6/1980 | Hindley et al. | 260/570.9 |
| 4,277,496 | 7/1981 | Los | 424/309 |
| 4,350,822 | 9/1982 | Albright et al. | 560/45 |
| 4,362,892 | 12/1982 | Hindley et al. | 564/374 |
| 4,555,516 | 11/1985 | Cross et al. | 514/326 |
| 4,559,336 | 12/1985 | Mueller | 514/211 |
| 4,578,390 | 3/1986 | Jensen et al. | 514/255 |
| 4,590,199 | 5/1986 | Coker et al. | 514/343 |
| 4,614,617 | 9/1986 | Mueller | 540/547 |
| 4,704,386 | 11/1987 | Mueller | 514/211 |
| 4,767,767 | 8/1988 | Foguet et al. | 514/313 |
| 4,839,369 | 6/1989 | Youssefyeh et al. | 514/314 |
| 4,937,373 | 6/1990 | Carson et al. | 560/56 |
| 5,087,743 | 2/1992 | Jansen et al. | 562/466 |
| 5,105,017 | 4/1992 | Diuard | 568/64 |
| 5,189,033 | 2/1993 | Tucker | 514/211 |
| 5,210,206 | 5/1993 | Morton et al. | 548/238 |
| 5,250,548 | 10/1993 | Winn et al. | 514/340 |
| 5,284,954 | 2/1994 | Wittenberger et al. | 546/276 |
| 5,314,883 | 5/1994 | Tanikawa et al. | 514/236.5 |
| 5,317,101 | 5/1994 | Tucker et al. | 540/488 |
| 5,324,743 | 6/1994 | Dillard et al. | 514/456 |
| 5,393,768 | 2/1995 | Dillard et al. | 514/381 |
| 5,409,930 | 4/1995 | Spada et al. | 514/248 |
| 5,420,270 | 5/1995 | Chandrakumar et al. | 540/488 |
| 5,441,950 | 8/1995 | Collins et al. | 514/211 |
| 5,530,157 | 6/1996 | Mewshaw et al. | 562/490 |

FOREIGN PATENT DOCUMENTS

| | | |
|---|---|---|
| 2111035 | 6/1994 | Canada . |
| 0475206 | 3/1992 | European Pat. Off. . |
| 0752421 | 1/1997 | European Pat. Off. . |
| 1560281 | 2/1980 | United Kingdom . |
| WO 96/03380 | 2/1996 | WIPO . |
| WO 96/06822 | 3/1996 | WIPO . |
| WO 96/11902 | 4/1996 | WIPO . |
| WO 97/00863 | 1/1997 | WIPO . |
| WO 97/00864 | 1/1997 | WIPO . |

OTHER PUBLICATIONS

Chem. Abstracts, vol. 91, No. 27, 1979, abstract 56831t, p. 691.

Albright et al., J. Med. Chem. 1983, 26, 1378–1393, Potential Antiatherosclerotic Agents. 2.$^1$ (Aralkylamino)– and (Alkylamino) benzoic Acid Analogues of Cetaben.

Brown et al., J. Med. Chem., 1989, 32, 807–825, Hydroxyacetophenone–Derived Antagonists of the Peptidoleukotrienes.

P. Feit et al., J. Med. Chem., 1970, 13, 1071–1075, Aminobenzoic Acid Diuretics. 1. 4–Halogeno–5–sulfamylmetanilic Acid Derivatives.

P. Nussbaumer et al., J Med. Chem., 1994, 37, 4079–4084, Novel Antiproliferative Agents Derived from Lavendustin A.

*Primary Examiner*—Mukund J. Shah
*Assistant Examiner*—Tamthom N. Truong
*Attorney, Agent, or Firm*—Kenneth F. Mitchell

[57] ABSTRACT

The invention relates to compounds of formula I and pharmaceutically acceptable salts and in vivo hydrolysable esters and amides thereof and processes for their preparation, their use as therapeutic agents and pharmaceutical compositions containing them.

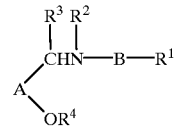

I

In formula I, A is a ring system in which the —CH($R^3$)N($R^2$)B—$R^1$ and —O$R^4$ groups are positioned in a 1,2 relationship to one another on ring carbon atoms. B is a ring system having $R^1$ in a 1,3 or 1,4 relationship with the —CH($R^3$)N($R^2$)— linking group. $R^2$ is hydrogen or $C_1$–$C_6$-alkyl, $R^3$ is hydrogen, methyl or ethyl, and $R^4$ is $C_1$–$C_6$-alkyl, $C_1$–$C_6$-cycloalkyl-$C_1$–$C_3$-alkyl, $C_3$–$C_7$-cycloalkyl, N-oxides of —N$R^2$, where chemically possible, or S-oxides of sulphur containing rings, where chemically possible. A, B, $R^1$, $R^2$, $R^3$ and $R^4$ may be substituted, as defined in the specification.

14 Claims, No Drawings

AROMATIC COMPOUNDS AND PHARMACEUTICAL COMPOSITIONS CONTAINING THEM

Aromatic compounds and pharmaceutical compositions containing them This invention relates to novel, aromatic compounds and pharmaceutically-acceptable salts thereof which possess useful pharmacological properties. More particularly the compounds of the invention are antagonists of the pain enhancing effects of E-type prostaglandins. The invention also relates to processes for the manufacture of the aromatic compounds and pharmaceutically-acceptable salts thereof; to novel pharmaceutical compositions containing them; and to use of the compounds in pain relief.

The compounds of the invention are useful in the treatment of pain such as the pain associated with joint conditions (such as rheumatoid arthritis and osteoarthritis), post-operative pain, post-partum pain, the pain associated with dental conditions (such as dental caries and gingivitis), the pain associated with burns (including sunburn), the treatment of bone disorders (such as osteoporosis, hypercalcaemia of malignancy and Paget's disease), the pain associated with sports injuries and sprains and all other painful conditions in which E-type prostaglandins wholly or in part play a pathophysiological role.

Non-steroidal anti-inflammatory drugs (NSAIDS) and opiates are the main classes of drugs in pain relief. However both possess undesirable side effects. NSAIDS are known to cause gastrointestinal irritation and opiates are known to be addictive.

We have now found a class of compounds structurally different to NSAIDS and opiates, and useful in relief of pain.

The compounds of the invention may also possess anti-inflammatory, anti-pyretic and anti-diarrhoeal properties and be effective in other conditions in which prostaglandin $E_2$ (PGE$_2$) wholly or in part plays a pathophysiological role.

The compound 2-[2-methoxybenzylamino]pyridine-5-carboxylic acid is disclosed in European Patent Application No. 0000816 (as example number 28 therein) and stated to be of value in the treatment of diabetes. The compound 4-[2-methoxybenzylamino]-benzoic acid is disclosed in U.S. Pat. No. 4,362,892 (as example number 8 therein) and stated to possess hypolipidaemic activity. The compounds 3-[2-methoxybenzylamino]-4-chloro-5-sulphamoylbenzoic acid and 3-[2,3-dimethoxybenzylamino]-4-chloro-5-sulphamoylbenzoic acid are disclosed by P. Feit et al., *J. Med. Chem.*, 1970, 13, 1071, as diuretics. The compound 5-[2,5-dimethoxybenzylamino]-2-hydroxybenzoic acid is disclosed by P. Nussbaumer et al., *J. Med. Chem.* 1994, 37, 4079, as an antiproliferative agent.

According to the invention there is provided a compound of the formula 1:

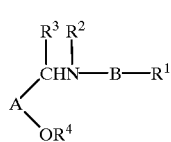

(I)

wherein:

A is an optionally substituted:
  phenyl, naphthyl, pyridyl, pyrazinyl, pyridazinyl, pyrimidyl, thienyl, thiazolyl, oxazolyl or thiadiazolyl having at least two adjacent ring carbon atoms; provided that the —CH(R$^3$)N(R$^2$)B—R$^1$ and —OR$^4$ groups are positioned in a 1,2 relationship to one another on ring carbon atoms and the ring atom positioned ortho to the OR$^4$ linking group (and therefore in the 3-position relative to the —CHR$^3$NR$^{2-}$ linking group) is not substituted;

B is an optionally substituted:
  phenyl, pyridyl, thiazolyl, oxazolyl, thienyl, thiadiazolyl, imidazolyl, pyrazinyl, pyridazinyl or pyrimidyl;

R$^1$ is positioned on ring B in a 1,3 or 1,4 relationship with the —CH(R$^3$)N(R$^2$)— linking group and is carboxy, carboxyC$_{1-3}$alkyl, tetrazolyl, tetrazolylC$_{1-3}$alkyl, tetronic acid, hydroxamic acid, sulphonic acid, or R$^1$ is of the formula —CONR$^a$R$^{a1}$ wherein R$^a$ is hydrogen or C$_{1-6}$alkyl and R$^{a1}$ is hydrogen, C$_{1-6}$alkyl (optionally substituted by halo, amino, C$_{1-4}$alkylamino, di-C$_{1-4}$alkylamino. hydroxy, nitro, cyano, trifluoromethyl, C$_{1-4}$alkoxy or C$_{1-4}$alkoxycarbonyl), C$_{2-6}$alkenyl (provided the double bond in not in the 1-position), C$_{2-6}$alkynyl (provided the triple bond is not in the 1-position), carboxyphenyl, 5- or 6-membered heterocyclylC$_{1-3}$alkyl, 5- or 6-membered heteroarylC$_{1-3}$alkyl, 5- or 6-membered heterocyclyl, or 5- or 6-membered heteroaryl or R$^a$ and R$^{a1}$ together with the amide nitrogen to which they are attached (NR$^a$R$^{a1}$) form an amino acid residue or ester thereof, or R$^1$ is of the formula —CONHSO$_2$R$^b$ wherein Rb is C$_{1-6}$alkyl (optionally substituted by halo, hydroxy, nitro, cyano, trifluoromethyl, C$_{1-4}$alkoxy, amino, C$_{1-4}$alkylamino, di-C$_{1-4}$alkyl amino or C$_{1-4}$alkoxycarbonyl), C$_{2-6}$alkenyl (provided the double bond is not in the 1-position), C$_{2-6}$alkynyl (provided the triple bond is not in the 1-position), 5- or 6-membered heterocyclylC$_{1-3}$alkyl, 5- or 6-membered heteroarylC$_{1-3}$alkyl, phenylC$_{1-3}$alkyl, 5- or 6-membered heterocyclyl, 5- or 6-membered heteroaryl or phenyl;

wherein any heterocyclyl or heteroaryl group in R$^{a1}$ is optionally substituted by halo, hydroxy, nitro, cyano, trifluoromethyl, C$_{1-4}$alkoxy or C$_{1-4}$alkoxycarbonyl and any phenyl heterocyclyl or heteroaryl group in R$^b$ is optionally substituted by halo, trifluoromethyl, nitro, hydroxy, amino, cyano, C$_{1-6}$alkoxy, C$_{1-6}$alkylS(O)p—(p is 0, 1 or 2), C$_{1-6}$alkyl carbamoyl, C$_{1-4}$alkylcarbamoyl, di(C$_{1-4}$alkyl)carbamoyl, C$_{2-6}$alkenyl, C$_{2-6}$alkynyl, C$_{1-4}$alkoxycarbonylamino. C$_{1-4}$alkanoylamino, C$_{1-4}$alkanoyl(N-C$_{1-4}$alkyl) amino, C$_{1-4}$alkanesulphonamido, benzenesulphonamido, aminosulphonyl, C$_{1-4}$alkylaminosulphonyl, di(C$_{1-4}$alkyl)aminosulphonyl, C$_{1-4}$alkoxycarbonyl, C$_{1-4}$alkanoyloxy, C$_{1-6}$alkanoyl, formylC$_{1-4}$alkyl, hydroxyiminoC$_{1-6}$alkyl, C$_{1-4}$alkoxyiminoC$_{1-6}$alkyl or C$_{1-6}$alkylcarbamoylamino, or R$^1$ is of the formula —SO2N(R$^c$)R$^{c1}$ wherein R$^c$ is hydrogen or C$_{14}$alkyl and R$^{c1}$ is hydrogen or C$_{1-4}$alkyl;

or R$^1$ is of the formula (IA), (IB) or (IC):

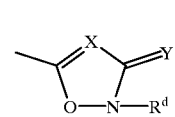

(IA)

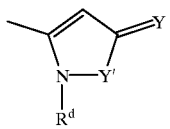

(IB)

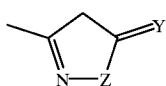

(IC)

wherein X is CH or nitrogen, Y is oxygen or sulphur, Y' is oxygen or $NR^d$ and Z is $CH_2$, $NR^d$ or oxygen provided that there is no more than one ring oxygen and there are at least two ring heteroatoms and wherein $R^d$ is hydrogen or $C_{1-4}$alkyl;

$R^2$ is hydrogen, $C_{1-6}$alkyl, optionally substituted by hydroxy, cyano or trifluoromethyl, $C_{2-6}$alkenyl (provided the double bond is not in the 1-position), $C_{2-6}$alkynyl (provided the triple bond is not in the 1-position), phenyl$C_{1-3}$alkyl or pyridyl$C_{1-3}$alkyl;

$R^3$ is hydrogen, methyl or ethyl;

$R^4$ is optionally substituted: $C_{1-6}$alkyl, $C_{3-7}$cycloalkyl$C_{1-3}$alkyl or $C_{3-7}$cycloalkyl; and N-oxides of $-NR^2$ where chemically possible;

and S-oxides of sulphur containing rings where chemically possible;

and pharmaceutically acceptable salts and in vivo hydrolysable esters and amides thereof;

excluding 2- [2-methoxybenzylamino]pyridine-5-carboxylic acid, 4-[2-methoxybenzylamino]benzoic acid, 3-[2-methoxybenzylamino]-4-chloro-5-sulphamoylbenzoic acid, 3-[2,3-dimethoxybenzylamino]-4-chloro-5-sulphamoylbenzoic acid and 5-[2,5-dimethoxybenzylamino]-2-hydroxybenzoic acid.

A 5- or 6-membered heteroaryl ring system is a monocyclic aryl ring system having 5 or 6 ring atoms wherein 1, 2 or 3 ring atoms are selected from nitrogen, oxygen and sulphur.

A 5- or 6-membered saturated or partially saturated heterocyclic ring is a ring system having 5 or 6 ring atoms wherein 1, 2 or 3 of the ring atoms are selected from nitrogen, oxygen and sulphur.

Particular 5- or 6-membered monocyclic heteroaryl rings include pyrrolyl, imidazolyl, pyrazolyl, isothiazolyl, isoxazolyl, pyridyl, pyrazinyl, pyrimidinyl, pyridazinyl, thiazolyl, thiadiazolyl, thienyl, furyl and oxazolyl.

Particular 5- or 6-membered saturated or partially saturated heterocyclic ring systems include pyrrolidinyl, pyrrolinyl, imidazolidinyl, pyrazolidinyl, piperidyl, piperazinyl and morpholinyl.

Particular substituents for ring carbon atoms in A (heterocyclyl and heteroaryl-rings) include halo, trifluoromethyl, nitro, hydroxy, amino, $C_{1-4}$alkylamino, di$C_{1-4}$alkylamino, cyano, $C_{1-6}$alkoxy, $C_{1-6}$alkylS(O)$_p$— (p is 0, 1 or 2), $C_{1-6}$alkyl (optionally substituted by hydroxy, amino, halo, nitro or cyano), $CF_3S(O)_p$—(p=0, 1 or 2), carbamoyl, $C_{1-4}$alkylcarbamoyl, di($C_{1-4}$alkyl)carbamoyl, $C_{2-6}$alkenyl, $C_{2-6}$alkynyl, $C_{1-4}$alkoxycarbonylamino, $C_{1-4}$alkanoylamino, $C_{1-4}$alkanoyl(N—$C_{1-4}$alkyl)amino, $C_{1-4}$alkanesulphonamido, benzenesulphonamido, aminosulphonyl, $C_{1-4}$alkylaminosulphonyl, $C_{1-4}$alkanoylaminosulphonyl, di($C_{1-4}$alkyl)aminosulphonyl, $C_{1-4}$alkoxycarbonyl, $C_{1-4}$alkanoyloxy, $C_{1-6}$alkanoyl, formyl$C_{1-4}$alkyl, trifluoro$C_{1-3}$alkylsulphonyl, hydroxyimino$C_{1-6}$alkyl, $C_{1-4}$alkoxyimino$C_{1-6}$alkyl and $C_{1-6}$alkylcarbamoylamino.

Where a ring nitrogen atom in A can be substituted without becoming quaternised, it is unsubstituted or substituted by $C_{1-4}$alkyl.

Particular substituents for ring carbon atoms in B include halo, trifluoromethyl, nitro, hydroxy, $C_{1-6}$alkoxy, $C_{1-6}$alkyl, amino, $C_{1-4}$alkylamino, di($C_{1-4}$alkyl)amino, cyano, $C_{1-6}$alkyl S(O)p—(p is 0, 1 or 2), carbamoyl, $C_{1-4}$alkylcarbamoyl and di($C_{1-4}$alkyl)carbamoyl.

Where a ring nitrogen atom in B can be substituted without becoming quaternised, it is unsubstituted or substituted by $C_{1-4}$alkyl.

The term alkyl when used herein includes straight chain and branched chain substituents for example methyl, ethyl, n-propyl, isopropyl, n-butyl and isobutyl and functional groups on alkyl chains may be anywhere on the chain, for example hydroxyimino$C_{1-6}$alkyl includes 1-(hydroxyimino) propyl and 2-(hydroxyimino)propyl.

$C_{1-6}$alkyl substituted by halo includes trifluoromethyl.

Amino acid residues formed from $R^a$ and $R^{a1}$ together with the nitrogen to which they are attached include residues (—NHCH(R)COOH) derived from naturally-occurring and non-naturally-occurring amino acids. Examples of, suitable amino acids include glycine, alanine, serine, threonine, phenylalanine, glutamic acid, tyrosine, lysine and dimethylglycine.

Suitable ring systems of the formula (IA), (IB), or (IC) include 5-oxo-4,5-dihydro-1,2,4-oxadiazol-3-yl, 3-oxo-2,3-dihydro-1,2,4-oxadiazol-5-yl, 3-thioxo-2,3-dihydro-1,2,4-oxadiazol-5-yl, 5-oxo-4,5-dihydro-1,3,4-oxadiazol-2-yl, 5-oxo-4,5-dihydro-1,2,4-triazol-3-yl, 5-thioxo-4,5-dihydro-1,3,4-oxadiazol-2-yl, 1,3,4-oxadiazol-2-yl, 3-hydroxy-2-methylpyrazol-5-yl, 3-oxo-2,3-dihydroisoxazol-5-yl, 5-oxo-1,5-dihydroisoxazol-3-yl and 5-oxo-2,3-dihydropyrazol-3-yl.

Examples of $C_{1-6}$alkoxycarbonyl are methoxycarbonyl, ethoxycarbonyl and t-butoxycarbonyl; examples of carboxy$C_{1-3}$alkyl are carboxymethyl, 2-carboxyethyl, 1-carboxyethyl and 3-carboxypropyl; examples of $C_{1-6}$alkoxycarbonyl$C_{1-3}$alkyl are methoxycarbonylmethyl, ethoxycarbonylmethyl and methoxycarbonylethyl; examples of tetrazolyl$C_{1-3}$alkyl are tetrazolylmethyl and 2-tetrazolylethyl; examples of $C_{1-4}$alkoxy are methoxy, ethoxy, propoxy and isopropoxy; examples of $C_{2-6}$alkenyl are vinyl and allyl; examples of $C_{2-6}$alkynyl are ethynyl and propynyl; examples of $C_{1-4}$alkanoyl are formyl, acetyl, propionyl and butyryl; examples of halo are fluoro, chloro, bromo and iodo; examples of $C_{1-4}$alkylamino are methylamino, ethylamino, propylamino and isopropylamino; examples of di($C_{1-4}$alkyl)amino are dimethylamino, diethylamino and ethylmethylamino; examples of $C_{1-6}$alkylS(O)$_p$- are methylthio, methylsulphinyl and methylsulphonyl; examples of $C_{1-4}$alkylcarbamoyl are methylcarbamoyl and ethylcarbamoyl; examples of di($C_{1-4}$alkyl)carbamoyl are dimethylcarbamoyl, diethylcarbamoyl and ethylmethylcarbamoyl; examples of $C_{1-6}$alkyl are methyl, ethyl, propyl and isopropyl; examples of $C_{1-4}$alkoxycarbonylamino are methoxycarbonylamino and ethoxycarbonylamino; examples of $C_{1-4}$alkanoylamino are acetamido and propionamido; examples of $C_{1-4}$alkanoyl (N—$C_{1-4}$alkyl)amino are N-methylacetamido and N-methylpropionamido; examples of $C_{1-4}$alkanesulphonamido are methanesulphonamido and ethanesulphonamido; examples of $C_{1-4}$alkylaminosulphonyl are methylaminosulphonyl and ethylaminosulphonyl;

examples of di($C_{1-4}$alkyl)aminosulphonyl are dimethylaminosulphonyl, diethylaminosulphonyl and ethylmethylaminosulphonyl; examples of $C_{1-4}$alkanoyloxy are acetyloxy and propionyloxy; examples of formyl$C_{1-4}$alkyl are formylmethyl and 2-formylethyl; examples of hydroxyimino$C_{1-6}$alkyl are hydroxyiminomethyl and 2-(hydroxyimino)ethyl; and examples of $C_{1-4}$alkoxyimino $C_{1-6}$alkyl are methoxyiminomethyl, ethoxyiminomethyl and 2-(methoxyimino)ethyl.

It will be understood that when formula I compounds contain a chiral centre, the compounds of the invention may exist in, and be isolated in, optically active or racemic form. The invention includes any optically active or racemic form of a compound of formula I which possesses pain-relieving properties. The synthesis of optically active forms may be carried out by standard techniques of organic chemistry well known in the art, for example by, resolution of a racemic form, by synthesis from optically active starting materials or by asymmetric synthesis. It will also be appreciated that certain compounds of formula I may exist as geometrical isomers. The invention includes any geometrical isomer of a compound of formula I which possesses pain-relieving properties.

It will also be understood that certain compounds of the present invention may exist in solvated, for example hydrated, as well as unsolvated forms. It is to be understood that the present invention encompasses all such solvated forms which possess the property of relieving pain.

It will further be understood that the present invention encompasses tautomers of the compounds of the formula (I).

Preferably A is optionally substituted:
phenyl, naphthyl, thiadiazolyl, thienyl, pyridyl or pyrimidyl.

Preferably B is optionally substituted:
pyridyl, phenyl, thiazolyl, thienyl, pyridazinyl, or oxazolyl.

Most preferably A is optionally substituted:
phenyl or thienyl.

Most preferably B is optionally substituted:
pyridyl, phenyl, thienyl, pyridazinyl or thiazolyl.

In particular A is optionally substituted phenyl.
In particular B is optionally substituted:
pyrid-2,5-diyl, pyridazin-3,6-diyl, phen-1,4-diyl or thien-2,5-diyl.

Most particularly B is optionally substituted pyridazin-3,6-diyl or pyrid-2,5-diyl.

Most preferably B is pyridazinyl.

Preferred optional substituents for ring carbon atoms in A, are halo, nitro, trifluoromethyl, cyano, amino, $C_{1-6}$alkoxy, carbamoyl, $C_{1-4}$alkylcarbamoyl, di($C_{1-4}$alkyl)carbamoyl, $C_{1-4}$alkanoylamino, $C_{1-6}$alkylS(O)$_{p^-}$, $C_{1-4}$alkanesulphonamido, benzenesulphonamido, $C_{1-6}$alkanoyl, $C_{1-4}$alkoxyimino$C_{1-4}$alkyl and hydroxyimino$C_{1-4}$alkyl.

Preferably, when A is a 6-membered ring, A is unsubstituted or substituted in the 4-position relative to the —OR$^4$ group.

Preferred optional substituents for ring carbon atoms of B are halo, trifluoromethyl, $C_{1-4}$alkyl, amino, $C_{1-4}$ alkylamino, di$C_{1-4}$alkylamino, nitro, hydroxy, $C_{1-6}$alkoxy and cyano.

Preferably A is unsubstituted or substituted by one substituent.

More preferably A is unsubstituted or substituted by bromo, methanesulphonyl, fluoro or chloro.

Most preferably A is unsubstituted or substituted by bromo or chloro.

Preferably B is unsubstituted or substituted by one substituent.

Most preferably B is unsubstituted.

Preferably R$^1$ is carboxy, carbamoyl or tetrazolyl or R$^1$ is of the formula —CONR$^a$R$^{a1}$ wherein R$^a$ is hydrogen or $C_{1-6}$alkyl and R$^{a1}$ is $C_{1-6}$alkyl optionally substituted by hydroxy, $C_{2-6}$alkenyl, 1-morpholinyl, 1-piperidinyl, 1-pyrrolidinyl, pyridyl$C_{1-3}$alkyl or R$^1$ is of the formula —CONHSO$_2$R$^b$ wherein R$^b$ is optionally substituted: $C_{1-6}$alkyl, phenyl or 5- or 6-membered heteroaryl.

In particular, R$^1$ is carboxy, tetrazolyl or of the formula —CONR$^a$R$^{a1}$ wherein R$^a$ is hydrogen and R$^{a1}$ is $C_{1-6}$alkyl optionally substituted by hydroxy or pyridylmethyl, or R$^1$ is of the formula —CONHSO$_2$R$^b$ wherein R$^b$ is $C_{1-6}$alkyl (optionally substituted by hydroxy or fluoro), phenyl (optionally substituted by acetamido), isoxazolyl (optionally substituted by methyl) or 1,3,4-thiadiazolyl (optionally substituted by acetamido).

Most preferably R$^1$ is carboxy, tetrazole or of the formula —CONHR$^{a1}$ wherein R$^{a1}$ is pyridylmethyl or $C_{1-4}$alkyl optionally substituted by hydroxy, or of the formula —CONHSO$_2$R$^b$ wherein R$^b$ is $C_{1-4}$ alkyl, 3,5-dimethylisoxazol-4-yl, or 5-acetamido-1,3,4-thiadiazol-2-yl.

In another aspect R$^1$ is carboxy, carbamoyl or tetrazolyl or R$^1$ is of the formula —CONR$^a$R$^{a1}$ wherein R$^a$ is hydrogen or $C_{1-6}$alkyl and R$^{a1}$ is $C_{11}$-alkyl optionally substituted by hydroxy, $C_{2-6}$alkenyl, 1-morpholinyl, 1-piperidinyl, 1-pyrrolidinyl, pyridyl$C_{1-3}$alkyl or R$^1$ is of the formula —CONHSO$_2$R$^b$ wherein R$^b$ is $C_{1-6}$alkyl or phenyl.

Preferably R$^2$ is hydrogen, methyl, ethyl, 2,2,2-trifluoroethyl, cyanomethyl, allyl or 3-propynyl.

More preferably R$^2$ is hydrogen, methyl, ethyl or propyl.

Yet more preferably R$^2$ is hydrogen or ethyl.

Most preferably R$^2$ is ethyl.

Preferably R$^3$ is hydrogen.

Preferably R$^4$ is optionally substituted by halo, hydroxy, $C_{1-4}$alkoxy, amino, carboxy, $C_{1-4}$ alkylS(O)p-(p=0, 1 or 2), carbamoyl, trifluoromethyl, oxo or cyano.

More preferably R$^4$ is optionally substituted by fluoro, chloro or bromo.

Most preferably R$^4$ is optionally substituted by fluoro, trifluoromethyl, cyano or hydroxy.

Preferably R$^4$ is $C_{1-4}$alkyl, $C_{3-6}$cycloalkyl or $C_{3-6}$cycloalkylmethyl.

More preferably R$^4$ is propyl, isobutyl, butyl, 2-ethylbutyl, 2(R)-methylbutyl, 2(S)-methylbutyl, 2,2,2-trifluoroethyl, cyclopentylmethyl, cyclopropylmethyl, cyclopropyl or cyclopentyl.

Most preferably R$^4$ is propyl, isobutyl, butyl, 2-ethylbutyl, cyclopentyl, cyclopropylmethyl or cyclopropyl.

A preferred class of compounds is that of the formula (II):

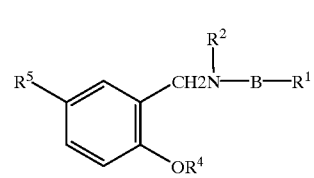

(II)

wherein
R$^1$ and R$^2$ are as hereinabove defined, R$^4$ is $C_{1-4}$alkyl $C_{3-6}$cycloalkyl or $C_{3-6}$ cycloalkylmethyl, R$^5$ is hydrogen or as hereinabove defined for substituents for ring carbon atoms in A, and B is phenyl, thienyl, pyridazinyl, pyridyl, or thiazolyl.

It is to be understood that, insofar as certain of the compounds of formula (I) defined above may exist in optically active or racemic forms, by virtue of the compounds of the formula (I) containing an asymmetric carbon atom, the invention includes in its definition of active ingredient any such optically active or racemic form which possesses pain relieving properties. The synthesis of optically active forms may be carried out by standard techniques of organic chemistry well known in the art, for example by synthesis from optically active starting materials or by resolution of a racemic form. Similarly, pain relieving properties may be evaluated using the standard laboratory techniques referred to hereinafter.

An in vivo hydrolysable ester of a compound of the formula (I) containing carboxy group is, for example, a pharmaceutically acceptable ester which is hydrolysed in the human or animal body to produce the parent acid, for example, a pharmaceutically acceptable ester formed with a (1–6C)alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halo (such as fluoro or chloro), (1–4C)alkyl (such as methyl) or (1–4C)alkoxy (such as ethoxy) group. The term also includes (x-acyloxyalkyl esters and related compounds which break down to give the parent hydroxy group. Examples of α-acyloxyalkyl esters include acetoxymethoxycarbonyl and 2,2-dimethylpropionyloxymethoxycarbonyl.

An in vivo hydrolysable ester of a compound of the formula (1) containing a hydroxy group is, for example, a pharmaceutically acceptable ester which is hydrolysed in the human or animal body to produce the parent alcohol. The term includes inorganic esters such as phosphate esters and a-acyloxyalkyl ethers and related compounds which as a result of the in vivo hydrolysis of the ester break down to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable value for an in vivo hydrolysable amide of a compound of the formula I containing a carboxy group is, for example, a N-(1–6C)alkyl or N,N-di-(1–6C)alkyl amide such as N-methyl, N-ethyl, N-propyl, N,N-dimethyl, N-ethyl-N-methyl or N,N-diethyl amide.

A suitable pharmaceutically-acceptable salt of a compound of the formula (I) is, for example, an acid-addition salt of a compound of the formula (I) which is sufficiently basic, for example an acid-addition salt with an inorganic or organic acid such as hydrochloric, hydrobromic, sulphuric, trifluoroacetic, citric or maleic acid; or, for example a salt of a compound of the formula (I) which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

In a further aspect the invention provides a process for preparing compounds of the formula (I) or pharmaceutically acceptable salts or in vivo hydrolysable amides or esters thereof, which comprises deprotecting a compound of the formula (III):

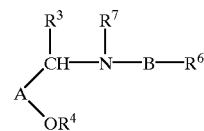

(III)

wherein $R^6$ is $R^1$ or protected $R^1$, $R^7$ is $R^2$ or protected $R^2$ and, $R^3$, $R^4$, A and B are as hereinabove defined, and any optional substituents are optionally protected and at least one protecting group is present;

and thereafter if necessary:

i) forming a pharmaceutically acceptable salt;
ii) forming an in vivo hydrolysable ester or amide;
iii) converting one optional substituent into another optional substituent.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1–4C)alkylsilyl group (especially trimethylsilyl or tert-butyldimethylsilyl), an aryldi-(1–4C)alkylsilyl group (especially dimethylphenylsilyl), a diaryl-(1–4C)alkylsilyl group (especially tert-butyldiphenylsilyl), a (1–4C)alkyl group (especially methyl), a (2–4C)alkenyl group (especially allyl), a (1–4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably, tetrabutylammonium fluoride. Alternatively an alkyl group may be removed, for example, by treatment with an alkali metal (1–4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1–4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2–4C) alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2–4C)alkanoyl group (especially acetyl), a (1–4C) alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

In another aspect the compounds of the formula (I) or (III) may be prepared by:

a) reducing a compound of the formula (IV)

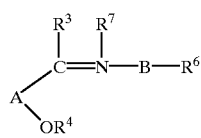

(IV)

b) when B is an activated heterocycle and $R^7$ is hydrogen or $C_{1-6}$alkyl reacting a compound of the formula (V) with a compound of the formula (VI):

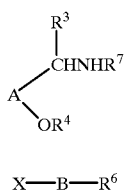

(V)

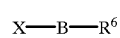

(VI)

c) reacting a compound of the formula (VII) with a compound of the formula (VIII):

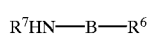

(VII)

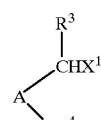

(VIII)

d) converting $X^2$ to $R^6$ in a compound of the formula (IX):

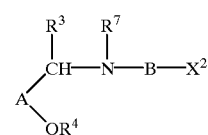

(IX)

e) when $R^7$ is other than hydrogen. reacting a compound of the formula $R^7X^3$ with a compound of the formula (X):

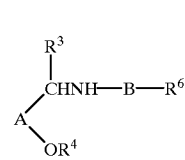

(X)

f) reacting a compound of the formula (XI) with a compound of the formula (XII):

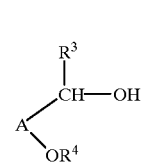

(XI)

(XII)

g) reacting a compound of the formula (XIII) with a compound of the formula (XIV):

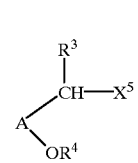

(XIII)

(XIV)

h) reacting a compound of the formula (XV) with a compound of the formula $X^7R^4$:

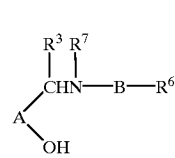

(XV)

wherein $R^3$, $R^4$, $R^7$, $R^9$, A and B are as hereinabove defined and X and $X^1$ are leaving groups, $X^2$ is a precursor of $R^7$, $X^3$ is a leaving group, $X^4$ is a removable activating group, $X^5$ is a leaving group, $X^6$ is an activating group and $X^7$ is a leaving group; and thereafter if necessary;

i) removing any protecting groups;
ii) forming a pharmaceutically acceptable salt;
iii) forming an in vivo hydrolysable ester or amide;
iv) converting an optional substituent into another optional substituent.

Particular values for leaving groups include halogen for example, chloro, bromo and iodo, sulphonates, for example tosylate, p-bromobenzenesulphonate, p-nitrobenzenesulphonate, methanesulphonate and triflate or phosphoric esters such as diarylphosphoric ester.

Compounds of the formula (IV) can be reduced using agents such as sodium borohydride or sodium cyanoborohydride. The compounds of the formula (IV) may be prepared by reacting a compound of the formula (VII) with a compound of the formula (XV)

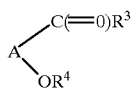

(XV)

wherein A, $R^3$ and $R^4$ are as hereinabove defined.

The reaction between compounds of the formulae (VII) and (XV) may be carried out under standard conditions known in the art for the formation an imine (Schiffs base), which can be reduced in situ. For example imine formation and reduction in situ may be carried out in an inert solvent such toluene or tetrahydrofuran. in the presence of a reducing agent such as sodium cyanoborohydride ($NaCNBH_3$) under acidic conditions (Synthesis 135, 1975; Org. Prep. Proceed. Int. 11, 201, 1979).

Compounds of the formulae (V) and (VI) may be reacted together under standard conditions for example, in an aprotic solvent such as DMF in the presence of a weak base, in a temperature range of ambient to 180° C. Suitable values for X include, halo, tosylate, mesylate and triflate. In particular X is chloro or bromo.

The compounds of the formulae (VII) and (VIII) may be reacted together under in an aprotic solvent such as DMF, in the presence of a base such as potassium carbonate or sodium hydride and in a temperature range of 0° C. to 100° C. Suitable values for $X^1$ include halo, tosylate, mesylate and triflate. In particular $X^1$ is bromo.

A precursor of $R^7$ is a group that can be converted into $R^7$.

Particular values for $X^2$ include cyano, carbamoyl, alkoxycarbonyl, carboxy and activated carboxy groups such as acid chlorides and activated esters.

The cyano group may be converted into a tetrazole ring by reacting. for example, with ammonium or tin azide in an aprotic solvent such as DMF, in a temperature range of 100° C. to 130° C. For further information on tetrazole synthesis see S. J. Wittenberger and B. J Donner JOC, 1993, 58, 4139–4141; B E Huff et al Tet. Lett. 1993, 50, 8011–8014, and J. V. Duncia et al, JOC 1991, 56, 2395–2400.

Alkoxycarbonyl may be converted into a carboxy group by acid or base hydrolysis. For example, base hydrolysis may be carried out in an organic solvent such as methanol or THF in a temperature range of ambient to 100° C., in the presence of sodium hydroxide or potassium hydroxide.

Acid hydrolysis may, for example, be carried out in neat formic acid or neat trifluoroacetic acid optionally in an inert organic solvent such as dichloromethane.

An alkoxycarbonyl or an activated carboxy group, such as an acid chloride or activated ester, or an acyl group such as an alkanoyl group may be converted to an amide group by reacting with the appropriate amine in an inert solvent such as DMF or dichloromethane, in a temperature range of 0° C. to 150° C., preferably around ambient temperature, in the presence of a base such as triethylamine.

The compounds of the formulae (X) and $R^7X^3$ may be reacted together in an aprotic solvent such as DMF in the presence of a base such as sodium carbonate or sodium hydride. Suitable values for $X^3$ are halo, tosylate, mesylate and triflate, in particular halo such as iodo.

The reaction between compounds of the formulae (XI) and (XII) is conveniently carried out under mild conditions known for the Mitsunobu reaction, for example in the presence of di ($C_{1-4}$alkyl)azocarboxylate and triphenylphosphine or $1^1,1^1$-(azodicarbonyl)dipiperidine and tributylphosphine (Tet. Lett. 34, 1993, 1639–1642) in an inert solvent such as toluene, benzene, tetrahydrofuran or diethylether, in particular toluene. Examples of removable activating groups are tert-butyloxycarbonyl and trifluoroacetyl.

Compounds of the formulae (XIII) and (XIV) are generally reacted together in the presence of a strong base such as sodium hydride, lithium diisopropylamine or LiN(SiMe3)2, in DMF or an etherial solvent such as ethyl ether or THF in a temperature range of −78° C. to ambient temperature. Suitable values for $X^5$ are halogen, or for example, methanesulphonate or tosylate. Examples of activating groups for $X^6$ include tert-butyloxycarbonyl, halogen and trifluoroacetyl.

The reaction between compounds of the formulae (XV) and $X^7R^4$ may be performed in an inert organic solvent such as acetone or DMF, in a temperature range of ambient temperature to 60° C. in the present of a mild base. Suitable leaving groups include tosylate, mesylate, triflate and halo. for example chloro or bromo. When $X^7$ is bromo, (XV) and $X^7R^4$ may be reacted together for example, in DMF, at ambient temperature in the presence of a base such as potassium carbonate. Alternatively a phase transfer system could be used. $X^7$ can be hydroxy which is activated in situ using the Mitsunobu reaction (O. Synthesis, 1981, 1.).

Compounds of the formula (XV) wherein $R^6$ is $R^1$ and $R^7$ is $R^2$ have pain-relieving properties in their own right.

Compounds of the formula (IV), (V), (VIII), (IX), (X), (XI), (XIII) and (XV) can be prepared using processes for the formation of the lower linking group —$OR^4$, similar to process h), from appropriate starting materials.

The compounds of the formula (IX) may be prepared using processes a), b), c), e), f), g) or h) from the appropriate starting material wherein $R^6$ is replaced with $X^2$.

The compounds of the formula (X) may be prepared by using any one of processes a), b), c), d), f), g) or h) from the appropriate starting materials wherein $R^7$ is hydrogen.

The compounds of the formula (XII) can readily be prepared from compounds of the formula (VII).

The compounds of the formulae (VI), (VII), (XII) and (XIV) are generally known in the art or can be made by methods analogous to or similar to those used in the examples or those known in the art for related compounds. Certain compounds of the formula (VI), wherein X is chloro or bromo, can be prepared by converting an oxo group in the ring system into chloro or bromo by reacting the oxo ring system with a chlorinating agent, such as sulphonyl chloride, phosphorous trichloride, phosphorous pentachloride or P(O)$Cl_3$ or brominating agent such as phosphorous tribromide or P(O)$Br_3$, in an inert aprotic solvent.

It is also possible to synthesise certain intermediates and even protected compounds using primarily ring synthesis. Here, reference is made to the compendium 'The Chemistry of Heterocyclic Compounds' E. C. Taylor and A. Weissberger (published by John Wiley and Sons) and 'Comprehensive Heterocyclic Chemistry', A. R Katritsky and C. W Rees (published by Pergamon Press).

Optional substituents may be converted into other optional substituents. For example an alkylthio group may be oxidised to an alkylsulphinyl or alkysulphonyl group, a nitro group reduced to an amino group, a hydroxy group alkylated to a methoxy group, or a bromo group replaced by an alkylthio group.

Various substituents may be introduced into compounds of the formulae (I) and (III) and intermediates in the preparation of compounds of the formulae (I) and (III), when appropriate, using standard methods known in the art. For example, an acyl group or alkyl group may be introduced into an activated benzene ring using Friedel-Crafts reactions, a formyl group by formylation with titanium tetrachloride and dichloromethyl ethyl ether, a nitro group by nitration with concentrated nitric acid concentrated sulphuric acid and bromination with bromine or tetra(n-butyl) ammonium tribromide.

It will be appreciated that. in certain steps in the reaction sequence to compounds of the formula (I), it will be necessary to protect certain functional groups in intermediates in order to prevent side reactions. Deprotection may be carried out at a convenient stage in the reaction sequence once protection is no longer required.

As stated hereinbefore compounds of the formula (I) are antagonists of the pain enhancing effects of E-type prostaglandins and of value in the relief of mild to moderate pain which, for example, accompanies inflammatory conditions such as rheumatoid arthritis and osteoarthritis. Certain properties of the compounds may be demonstrated using the test procedures set out below:

(a) an in-vitro guinea pig ileum assay which assesses the inhibitory properties of a test compound against $PGE_2$-induced contractions of the ileum; ileum was immersed in oxygenated Krebs solution containing indomethacin (4 $\mu$g/ml) and atropine (1 $\mu$M) and which was maintained at 37° C.; the ileum was subject to a tension of 1 g; a control dose response curve for $PGE_2$-induced contraction of the ileum was obtained; test compound (dissolved in dimethylsulphoxide) was added to the Krebs solution and a dose response curve for the $PGE_2$-induced contraction of the ileum in the presence of the test compound was obtained: the $pA_2$ value for the test compound was calculated;

(b) an in-vivo assay in mice which assesses the inhibitory properties of a test compound against abdominal constriction response induced by the intraperitoneal administration of a noxious agent such as dilute acetic acid or phenylbenzoquinone (hereinafter PBQ) using the procedure disclosed in European Patent Application No. 0218077.

Although the pharmacological properties of the compounds of the formula I vary with structural change as expected, in general activity possessed by compounds of the formula I may be demonstrated at the following concentrations or doses in one or more of the above-mentioned Tests (a) and (b):

Test (a): $pA_2 > 5.3$;

Test (b): $ED_{30}$ in the range, for example, 0.01–100 mg/kg orally.

No overt toxicity or other untoward effects were noted in Test (b) when compounds of the formula I are administered at several multiples of their minimum inhibitory dose.

Prostaglandin receptors and in particular receptors for $PGE_2$ have been tentatively characterised by Kennedy etal. (Advances in Prostaglandin, Thromboxane and Leukotriene Research, 1983, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did possess SC-19220 sensitive mediated effects were said to possess $EP_1$ receptors. Based on this compounds of the present invention, possessing activity in Test (a), are $EP_1$ antagonists.

According to a further feature of the invention there is provided a pharmaceutical composition which comprises a compound of the formula (I) or an in-vivo hydrolysable ester thereof or an amide thereof, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel, spray or aqueous or oily solution or suspension; for nasal use, for example a snuff, nasal spray or nasal drops; for vaginal or rectal use, for example a suppository or rectal spray; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a compound of the formula (I) or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition.

According to a further feature of the invention there is provided a compound of the formula (1) or an in-vivo hydrolysable ester or amide or a pharmaceutically-acceptable salt thereof, for use in a method of treatment of the animal (including human) body by therapy.

According to a further feature of the invention there is provided the use of a compound of the formula I, or an in-vivo hydrolysable ester or amide or a pharmaceutically-acceptable salt thereof, in the manufacture of a medicament for use in the relief of pain in the animal (including human) body.

According to a further feature of the invention there is provided a method for the relief of pain in the animal (including human) body in need of such treatment which comprises administering to said body an effective amount of a compound of the formula I, or an in-vivo hydrolysable ester or amide or a pharmaceutically-acceptable salt thereof.

As mentioned above, a compound of the formula (I) is useful in treating the pain which, for example, accompanies inflammatory conditions such as rheumatoid arthritis and osteoarthritis. In using a compound of the formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.05 mg to 30 mg per kg body weight will generally be used. Similarly, for administration by inhalation, a dose in the range, for example, 0.05 mg to 25 mg per kg body weight will be used.

Although the compounds of the formula (I) are primarily of value as therapeutic agents for use in warm-blooded animals (including man), they are also useful whenever it is required to antagonise the effects of $PGE_2$ at the $EP_1$ receptor, based on test a). Thus, they are useful as pharmacological standards for use in the development of new biological tests and in the search for new pharmacological agents.

By virtue of their ability to relieve pain, the compounds of the formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the formula (I), or an in-vivo hydrolysable ester or amide or pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with other anti-inflammatory agents such as an inhibitor of the enzyme 5-lipoxygenase (such as those disclosed in European Patent Applications Nos. 0351194, 0375368, 0375404, 0375452, 0375457, 0381375, 0385662, 0385663, 0385679, 0385680).

The compounds of the formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compositions of the invention may in addition contain one or more other therapeutic or prophylactic agents known to be of value for the treatment of pain. Thus for example, a known opiate pain-killer (such as dextropropoxyphene, dehydrocodeine or codeine) or an antagonist of other pain or inflammation mediators, such as bradykinin, takykinin and calcitonin gene related peptides (CGRP), or an alpha2-adrenoceptor agonist, a $GABA_B$ receptor agonist, a calcium channel blocker, a sodium channel blocker, a $CCK_B$ receptor antagonist, a neurokinin antagonist or an antagonist and modulator of the action of glutamate at the NMDA receptor may usefully also be present in a pharmaceutical composition of the invention.

The compounds of the present invention may also be administered in bone diseases such as osteoporosis with calcitonin and bisphosphonates.

The invention will now be illustrated in the following non-limiting Examples in which, unless otherwise stated:

(i) evaporations were carried out by rotary evaporations in vacuo and work-up procedures were carried out after removal or residual solids by filtration;

(ii) yields are given for illustration only and are not necessarily the maximum attainable;

(iii) the end-products of the formula I have satisfactory microanalysis and their structures were generally confirmed by NMR and mass spectral techniques;

(iv) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(v) the following abbreviations have been used:
DMF N,N-dimethylformamide;
THF tetrahydrofuran,
DMSO dimethylsulphoxide,
TLC thin layer chromatography,
MPLC medium pressure liquid chromatography.

EXAMPLE 1

2-[N-(5-Bromo-2-propoxybenzyl)-N-ethylamino] pyridine-5-carboxylic Acid

A solution of methyl 2-[N-(5-bromo-2-propoxybenzyl)-N-ethylamino]pyridine-5-carboxylate (reference example 1) (0.12 g, 0.29 mmol) in THF (3 ml) and methanol (3 ml) was treated with aqueous sodium hydroxide (1N, 1.8 ml). The reaction was heated to 40° C. for 18 hours. The solvent was then evaporated off and the residue diluted with water (3 ml) and acidified with acetic acid (1N, 3 ml). The solid was filtered off to give the title compound (0.1 g, 88%) as a white solid.

MS (Cl+): 393/395 $(M+H)^+$.

NMR (200 MHz, DMSO-d6) δ: 1.0 (t, J=7 Hz, 3H); 1.12 (t, J=7 Hz, 3H); 1.75 (m, 2H); 3.6 (q, J=7 Hz, 2H); 3.98 (t, J=7 Hz, 2H); 4.73 (s, 2H); 6.65 (d, J=9 Hz, 1H); 7.02 (m, 2H); 7.4 (dd, J=2, 9 Hz, 1H); 7.92 (dd, J=2,9 Hz, 1H); 8.6 (d, J=2 Hz, 1H).

EXAMPLE 2

2-[N-(5-Bromo-2-(2-methyl)propoxybenzyl)-N-ethylamino]-5-pyridinecarboxylic Acid The title compound was prepared using a similar method to that of example 1 except using the appropriate ester (reference example 2).

MS (CI+); 407 $(M+H)^+$.

NMR (250 MHz, DMSO-$d_6$) 67 : 1.0 (d, J=6 Hz, 6H), 1.05 (t, J=7 Hz, 3H), 2.02 (m, 1H); 3.59 (q, J=7 Hz, 2H), 3.8 (d, J=6 Hz, 2H), 4.75 (s, 2H); 6.64 (d, J=9 Hz, 1H), 6.96 (d, J=9 Hz, 1H); 7.05 (d, J=2 Hz, 1H); 7.36 (dd, J=2.9 Hz, 1H); 7.9 (dd, J=2,9 Hz, 1H); 8.61 (d, J=2 Hz, 1H); 12.35 (bs, 1H).

EXAMPLE 3

6-[N-(5-Bromo-2-(cyclopropylmethoxy)benzyl)-N-ethylamino]pyridazine-3-carboxylic Acid The title compound was prepared using a similar method to that of example 1 except using the appropriate butyl ester (reference example 4).

mp 73–80° C.

MS (FAB+): 406 $(M+H)^+$.

NMR (200 MHz, DMSO-$d_6$+HOAc-d4) δ 0.15 (m, 2H); 0.38 (m, 2H); 1.02 (m, 4H); 3.55 (q, J=7 Hz, 2H); 3.7 (d, J=7 Hz, 2H); 4.68 (s, 2H); 6.78 (m, 1H); 7.0 (m, 2H); 7.22 (d, J=9 Hz, 1H); 7.5 (d, J=9 Hz, 1H).

EXAMPLE 4

2-[N-(5-Bromo-2-(cyclopentylmethoxy)benzyl)-N-ethylamino]pyridine-5-carboxylic Acid A solution of methyl 2-[N-(5-bromo-2-(cyclopentylmethoxy)benzyl)-N-ethylamino]pyridine-5- carboxylate (see reference example 5) (0.37 g, 0.83 mmol) in THF (4 ml) and methanol (4 ml) was treated with 1N aqueous sodium hydroxide solution (4 ml). The reaction was heated at 40° C. for 18 hours. The solvents were evaporated at reduced pressure and the residue was acidified with 1N acetic acid (4 ml) and allowed to stir for 2 days. The precipitate was filtered, washed with water and dried in vacuo at 45° C. to give the title compound as a white solid (0.32 g, 89%).

MS (ESP+): 433 (M+H)+

NMR (200 MHz, DMSO-$d_6$) δ: 1.2 (t, J=7 Hz, 3H), 1.35 (m, 2H); 1.58 (m, 4H); 1.75 (m, 2H); 2.30 (m, 1H); 3.60 (q, J=7 Hz, 2H); 3.9 (d, J=7 Hz, 2H); 4.74 (s, 2H); 6.65 (d, J=9 Hz, 1H), 6.98 (d, J=9 Hz, 1H); 7.10 (d, J=2 Hz, 1H); 7.88 (dd, J=2, 9 Hz, 1H); 7.92 (d=2, 9 Hz, 1H); 8.62 (d, J=2 Hz, 1H); 12.4 (vbs. approx. 1H).

EXAMPLE 5

6-[N-(5-Bromo-2-propoxybenzyl)-N-ethylamino] pyridazine-3-carboxylic Acid

The title compound was prepared from butyl 6-[N-(5-bromo-2-propoxybenzyl)-N-ethylamino]pyridazine-3-carboxylate (reference example 6) using a similar method to that of example 1.

MS (ESP+): 394/396 (M+H)+.

NMR (200 MHz, DMSO-$d_6$) δ: 0.97 (t, J=6.7 Hz, 3H); 1.16 (t, J 6.7 Hz, 3H); 1.73 (m, J=6.7 Hz, 2H), 3.7 (q, J=6.7 Hz, 2H); 3.98 (t, J=6.7 Hz, 2H); 4.82 (s, 2H), 7.0 (d, J=9.3 Hz, 1H); 7.12 (d, J=9.3 Hz, 1H); 7.17 (d, J=2.0 Hz, 1H); 7.40 (dd, J=2.0, 10.0 Hz, 1H); 7.83 (d, J=10.0 Hz, 1H).

EXAMPLE 6

6-[N-(5-Bromo-2-n-butoxybenzyl)-N-ethylamino] pyridazine-3-carboxylic Acid

The title compound was prepared from butyl 6-[N-(5-bromo-2-n-butoxybenzyl)-N-ethylamino]pyridazine-3-carboxylate (reference example 7) using a similar method to that of example 1.

MS (ESP+): 408/410 (M+H)+.

NMR (200 MHz, DMSO-$d_6$) δ: 0.9 (t, J=6.7 Hz, 3H); 1.14 (t, J=6.7 Hz, 3H); 1.40 (m, J=6.7 Hz, 2H); 1.67 (m, J=6.7 Hz, 2H); 3.67 (q, J=6.7 Hz, 2H); 4.00 (t, J=6.7 Hz, 2H); 4.8 (s, 2H); 7.0 (d, J=8.3, 1H); 7.11 (d, J=10.0 Hz, 1H); 7.15 (d, J=1.7 Hz, 1H); 7.40 (dd, J=1.7, 8.3 Hz, 1H); 7.84 (d, J=10.0 Hz, 1H).

EXAMPLE 7

N-(3,5-Dimethylisoxazol-4-ylsulphonyl)-6-[N-(5-bromo-2-(cyclopropylmethoxy)benzyl)-N-ethylamino]pyridazine-3-carboxamide A solution of 6-[N-(5-bromo-2-(cyclopropylmethoxy) benzyl)-N-ethylamino]-pyridazine-3-carboxylic acid (example 3) (0.166 g. 0.409 mmol) in DMF (4 ml) was treated with 3,5-dimethyl-4-sulfonamidoisoxazole (0.08 g, 0.455 mmol), dimethylaminopyridine (0.15 g, 1.23 mmol) and 1-(3-dimethylaminopropyl)-3-ethylcarbodiimidehydrochloride (0.12 g, 0.627 mmol). The reaction was stirred at ambient temperature overnight. TLC (10% MeOH/$CH_2Cl_2$+1% HOAc) revealed the reaction had not gone to completion. Further portions of dimethylaminopyridine (0.05 g, 0.409 mmol) and 1-(3-dimethylaminopropyl)-3-ethylcarbodiimidehydrochloride (0.08 g, 0.418 mmol) were added and the reaction stirred at ambient temperature for 60 hours. The reaction mixture was partitioned between water and ethyl acetate. The organic layer was dried ($MgSO_4$) and evaporated and the residue was purified by chromatography (eluant: methanol/dichloromethane/acetic acid) to give the title compound as a foam (0.073 g).

MS (ESP+): 564 (M+H)+.

NMR (200 MHz, DMSO-$d_6$) δ: 0.3 (m, 2H); 0.53 (m, 2H); 1.55 (m, 4H); 2.40 (s, 3H); 2.70 (s, 3H); 3.70 (q, J=7 Hz, 2H); 3.87 (d, J=7 Hz, 2H); 4.85 (s, 2H); 6.98 (d, J=9 Hz, 1H); 7.22 (d, J=2 Hz, 1H); 7.24 (d, J=9 Hz, 1H); 7.39 (dd, J=2, 9 Hz, 1H); 7.83 (d, J=9 Hz, 1H).

EXAMPLE 8

The compounds in the following table were prepared using a similar method to that of Example 7 from the appropriate carboxylic acid and the appropriate sulphonamide compound.

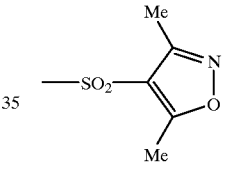

| $R^1$ | $R^2$ | MS ES+ (MH)+ | Foot-note |
|---|---|---|---|
| 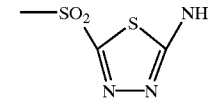 | —$CH_2CH(Me)CH_3$ | 522 | a |
| 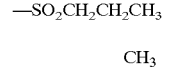 | " | 568 | b |
| —$SO_2CH_2CH_2CH_3$ | " | 469 | c |
| 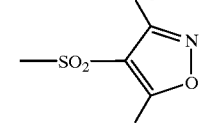 | cyclopentyl | 534/536 | d |
| —$SO_2CF_3$ | " | 507/509 | e |
| —$SO_2CH_2CH_2CH_3$ | cyclobutylmethyl | 480 | f |
| 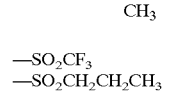 | cyclobutylmethyl | 534 | g |

Footnotes
a) NMR (200 MHz, DMSO-$d_6$)δ: 0.97 (d, 6H); 1.15 (t, 3H); 2.02 (m, 1H); 2.40 (s, 3H); 2.69 (s, 3H); 3.70 (q, 2H); 3.80 (d, 2H); 4.85 (s, 2H); 7.03 (m, 2H); 7.20 (d, 1H); 7.27 (dd, 1H); 7.82 (d, 1H).

Elemental Analysis: $C_{23}H_{28}ClN_5O_5S + 0.13$ mole toluene

|   | Theory (%) | Found (%) |
|---|---|---|
| C | 53.3 | 53.4 |
| H | 5.5 | 5.5 |
| N | 13.1 | 12.7 | b) NMR (200 MHz, DMSO-$d_6$) δ: 0.95 (d, 6H); 1.14 (t, 3H); 2.00 (m, 1H); 2.23 (s, 3H); 3.67 (q, 2H); 3.80 (d, 2H); 4.83 (s, 2H); 7.04 (d,) J=8 Hz, 1H); 7.14 (d, J=3 Hz, 1H); 7.28 (dd, J=8, 3 Hz, 1H); 7.57 (d, J=9 Hz, 1H); 8.05 (d, J=9 Hz, 1H); 12.84 (S, 1H).

Elemental Analysis: $C_{22}H_{26}ClN_7O_5S_2 + 0.1$ mole $CH_2Cl_2 + 0.2$ mole $H_2O$.

|   | Theory (%) | Found (%) |
|---|---|---|
| C | 45.8 | 45.4 |
| H | 4.6 | 4.5 |
| N | 16.9 | 16.8 | m.p. 240–242° C.

c) NMR (200 MHz, DMSO-$d_6$) δ: 1.00 (m, 9H), 1.15 (t, 3H); 1.75 (m, 2H); 2.03 (m, 1H); 3.45 (t, 2H); 3.70 (q, 2H); 3.81 (d, 2H); 4.86 (s, 2H); 7.03 (m, 2H); 7.20 (d, 1H); 7.27 (dd, 1H); 7.87 d, 1H).

Elemental Analysis: $C_{21}H_{29}ClN_4O_4S$

|   | Theory (%) | Found (%) |
|---|---|---|
| C | 53.8 | 53.9 |
| H | 6.2 | 6.2 |
| N | 11.9 | 11.9 | d) M.S. (ESP+): 534/536 (MH+).

NMR (200 MHz, DMSO-$d_6$ δ: 1.13(t, 3H); 1.65(br, m); 1.88(br m, 2H); 2.38(s, 3H); 2.68(s, 3H); 3.65(q, 2H); 4.76 (s, 2H); 4.85(m, 1H); 7.00(d, 1H); 7.03(d, 1H); 7.18(d, 1H); 7.24(dd, 1H); 7.82(d, 1H);.

e) M.S. (ESP+): 507/509 (MH+).

NMR (200 MHz, DMSO-$d_6$) δ: 1.11 (t, 3H), 1.60 (br m, 6H); 1.88 (m, 2H); 3.63 (q, 2H); 4.75 (s, 2H); 4.85 (m, 1H); 7.02(d, 1H); 7.30 (m, 2H); 7.88 (d, 2H); 8.20 (d, 2H).

f) M.p. 111–113° C.

NMR (MHz, DMSO-$d_6$) δ: 0.92(t, 3H); 1.1(t, 3H); 1.5–2.2 (m, 8H); 2.65(m, 1H); 3.25(m, 2H); 3.68 (q, 2H); 3.95 (d, 2H); 4.8 (s, 2H); 7.0(m, 2H); 7.15(d, 1H); 7.25(dd, 1H); 7.82 (d, 1H).

Elemental Analysis: $C_{22}H_{29}ClSN_4O_4 \cdot 0.75 H_2O$

|   | Theory (%) | Found (%) |
|---|---|---|
| C | 53.4 | 53.3 |
| H | 6.2 | 5.8 |
| N | 11.3 | 11.4 | g) M.p. 140–142° C.,

NMR (MHz, DMSO-$d_6$) δ: 1.1(t, 3H); 1.75–2.2 (m, 6H); 2.25(s, 3H); 2.55(s, 3H); 2.70(m, 1H); 3.65 (q, 2H); 4.0 (d, 2H); 4.75 (s, 2H); 7.0(m, 3H); 7.25(dd, 1H); 7.8 (d, 1H).

Elemental Analysis: $C_{24}H_{28}ClN_5O_5 \cdot H_2O$

|   | Theory (%) | Found (%) |
|---|---|---|
| C | 52.2 | 51.8 |
| H | 65.4 | 5.0 |
| N | 12.7 | 12.5 |

EXAMPLE 9

6-[N-(5-Bromo-2-(2-methylpropoxy)benzyl)-N-ethylamino]pyridazine-3-carboxylic Acid Butyl 6-[N-(5-bromo-2-(2-methylpropoxy)benzyl)-N-ethylamino]pyridazine-3-carboxylate (reference example 10) (0.22 g 0.47 mmol) in THF (3 ml) and methanol (3 ml) was treated with a 1N solution of aqueous sodium hydroxide (3 ml) and left at ambient temperature for 1.5 hours (after which time TLC (1:1 diethyl ether/hexane) indicated that none of the ester remained). The reaction mixture was evaporated to low bulk, taken up in a little water and acidified with acetic acid to produce a gum. The gum did not solidify so it was extracted with ethyl acetate (×2) and the combined extracts washed with brine, dried (MgSO$_4$) and evaporated to give a gum. The gum was evaporated from toluene and dichloromethane to give the title compound as a foam (140 mg 73%).

MS (CI$^+$): 408,410 (M+H)$^+$. MS (EI$^+$): 408,410 (M+H)$^+$.

NMR (200 MHz, DMSO-$d_6$) δ:1.00(d, J=10 Hz, 6H); 1.16(t, J=8.3 Hz, 3H); 1.93–2.15 (m, 1H); 3.69(q, J=8.3 Hz, 2H); 3.80(d, J=6.67 Hz, 2H); 4.84 (s, 2H); 6.98 (d, J=10 Hz, 1H); 7.12, (m,2H); 7.40 (dd, J=2, 8.3 Hz, 1H); 7.84 (d, J=10 Hz, 1H).

EXAMPLE 10

6-[N-(5-Chloro-2-(2-methylpropoxy)benzyl)-N-ethylamino]pyridazine-3-carboxylic Acid The title compound was prepared by hydrolysing butyl 6-[N-(5-chloro-2-(2-methylpropoxy)benzyl)-N-ethylamino] pyridazine-3-carboxylate (reference example 12) using a similar method to that of example 1.

NMR (250 MHz, DMSO-$d_6$) δ: 1.00 (d, 6H), 1.15 (t, 3H); 2.04 (m, 1H); 3.69 (q, 2H); 3.80 (d, 2H); 4.84 (s, 2H); 7.03 (m, 2H); 7.11 (d, 1H); 7.27 (dd, 1H); 7.83 (d, 1H).

MS (ES$^-$): 362 (M–H)$^-$.

Elemental Analysis: $C_{18}H_{22}ClN_3O_3$

|   | Theory (%) | Found (%) |
|---|---|---|
| C | 59.4 | 59.4 |
| H | 6.1 | 5.9 |
| N | 11.5 | 11.4 | m.p. 132–134° C.
MS (Cl+): 181 (M+H)$^+$

EXAMPLE 11

6-[N-(5-Bromo-2-(cyclopropylmethoxy)benzyl)-N-ethyl]pyridazine-3-carboxamide

N-Ethyl-5-bromo-2-(cyclopropylmethoxy)benzylamine (reference example 13) (12.56 g) was dissolved in NMP (59 ml) under argon. 6-Chloropyridazine-3-carboxamide (6.17 g, 3.9 mmol) and sodium bicarbonate (8.24 g, 98 mmol)

were added and the mixture heated to 110° C. for 24 hours. The mixture was then cooled and diluted with ethyl acetate and poured into a mixture of saturated aqueous ammonium chloride and 1N hydrochloric acid (50 ml). The white precipitate that formed was filtered off and washed with ethyl acetate and diethyl ether to give the title compound which was dried in a vacuum oven at 55° C. (11.46 g, 72.1%).

NMR (200 MHz, DMSO-$d_6$) δ: 0.34, (m, 2H); 0.55 (m, 2H); 1.17 (m, 4H); 3.69 (q, 2H); 3.88 (d, 2H); 4.80 (s, 2H); 6.96 (d, 1H); 7.15 (m, 2H); 7.37 (dd, 1H); 7.42 (brs, 1H); 7.84 (d, 1H); 8.14 (brs, 1H).

MS (ESP+): 405 (M+H)$^-$

EXAMPLE 12

5-[6-(N-[5-Bromo-2-(cyclopropylmethoxy)benzyl]-N-ethylamino)pyridazin-3-yl]tetrazole 6-[N-(5-Bromo-2-(cyclopropylmethoxy)benzyl)-N-ethylamino]-3-cyanopyridazine (reference example 14) (1.63 g) was dissolved in dimethylacetamide (DMA) (17 mls) under argon. Triethylamine hydrochloride (0.87 g, 6.3 mmol) and sodium azide (0.82 g, 12.6 mmol) were added and the mixture heated at 95–110° C. for 3 hours. It was then cooled and partitioned between saturated aqueous ammonium chloride and ethyl acetate. The organic layer was washed with 10% 2N HCl saturated aqueous ammonium chloride (×2) and brine (×2), dried over $Na_2SO_4$, filtered and evaporated. The residue was recrystallised from acetonitrile to give the title product (1.34 g, 74.0%).

NMR (200 MHz, $DMSO_6$) δ: 0.34 (m, 2H); 0.56 (m, 2H); 1.20 (m, 4H); 3.74 (q, 2H); 3.88 (d, 2H); 4.84 (s, 2H); 6.96 (d, 1H); 7.25 (d, 1H); 7.29 (d, 1H); 7.37 (dd, 1H); 8.03 (d, 1H).

Elemental Analysis: $C_{18}H_{20}BrN_7O$

|   | Theory (%) | Found (%) |
|---|---|---|
| C | 50.2 | 50.2 |
| H | 4.7 | 4.8 |
| N | 22.8 | 22.8 |

MS (ESP$^+$): 430 M+H)$^+$.

EXAMPLE 13

5-(6-[N-(5-Chloro-2-(2-methylpropoxy)benzyl)-N-ethylamino]pyridazin-3-)tetrazole The title compound was prepared from 6-[N-(5-chloro-2-(2-methylpropoxy)benzyl)-N-ethylamino]-3-cyanopyridazine (reference example 15) using a similar method to that of example 12.

NMR (200 MHz, DMSO-$d_6$) δ: 0.99 (d, 6H); 1.18 (t, 3H); 2.04 (m, 1H); 3.72 (q, 2H); 3.82 (d, 2H); 4.86 (s, 2H); 7.04 (d, 1H); 7.09 (d, 1H); 7.27 (m, 2H); 8.03 (d, 1H).

Elemental Analysis: $C_{18}H_{22}ClN_7O$

|   | Theory (%) | Found (%) |
|---|---|---|
| C | 55.7 | 55.6 |
| H | 5.7 | 5.7 |
| N | 25.3 | 24.9 |

MS (ES$^+$): 388 (M+H)$^+$. m.p. 204–206° C.

EXAMPLE 14

N-Propanesulphonyl-6-[N-(5-bromo-2-(cyclopropylmethoxy)benzyl)-N-ethylamino]pyridazine-3-carboxamide 6-[N-(5-Bromo-2-(cyclopropylmethoxy)benzyl)-N-ethylamine]pyridazine-3-carboxylic acid (example 3) (1.0 g, 2.46 mmol) was mixed with propylsulphonamide (0.32 g, 2.6 mmol), 4-(dimethylamino)pyridine (0.90 g, 7.38 mmol) and 1-(3-dimethylaminopropyl)-3-ethylcarboxiimide hydrochloride (0.71 g, 3.7 mmol) under argon. DMF (12.0 ml) was added and the mixture stirred at ambient temperature overnight.

The reaction mixture was then poured into saturated aqueous ammonium chloride and extracted with ethyl acetate (×2). The combined organic extracts were washed with 5% 2N HCl in saturated aqueous ammonium chloride, saturated aqueous sodium bicarbonate (×1) and brine (×1), dried over $Na_2SO_4$ filtered and evaporated. The residue was purified by MPLC using 2.5% IPA/dichloromethane+0.2% acetic acid. Fractions containing the title product were evaporated and the residue codistilled with toluene, isohexane and finally ether so that the title product was obtained as a white foam on drying under high vacuum. (1.00 g, 79.4%).

NMR (200 MHz, DMSO-$d_6$) δ: 0.30, (m, 2H); 0.55 (m, 2H); 1.00 (t, 3H); 1.16 (m, 4H); 1.75 (m, 2H); 3.45 (t, 3H); 3.73 (q, 2H); 3.87 (d, J=7.5 Hz, 2H); 4.85 (s, 2H); 6.97 (d, J=8.3 Hz, 1H); 7.18 (d, J=3.1 Hz, 1H); 7.24 (d, J=8.7 Hz, 1H); 7.39 (dd, J-8.3. 3.1 Hz, 1H); 7.86 (d, J=8.7 Hz, 1H).

Elemental Analysis: $C_{21}H_{27}BrN_4O_4S$.

|   | Theory (%) | Found (%) |
|---|---|---|
| C | 49.3 | 49.7 |
| H | 5.3 | 5.6 |
| N | 11.0 | 10.7 |

EXAMPLE 15

6-[N-(5-Bromo-2-(2-hydroxy-3,3,3-trifluoropropoxy)benzyl)-N-ethylamino]pyridazine-3-carboxylic Acid The title compound was prepared from the n-butyl ester (reference example 16) using a similar method to that of example 1.

NMR: (250 Mhz, DMSO-$d_6$) δ: 1.15 (t, 3H); 3.68 (g, zH); 4.20 (m, 2H); 4.44 (m, 1H); 4.89 (s, 2H); 7.08 (m, 3H), 7.4 (dd, 1H), 87.83 (d, 1H).

MS: 463 (M+H)$^+$.

EXAMPLE 16

5-[6-(N-[2-(Cyclopropylmethoxy)-5-methanesulphonylbenzyl]-N-ethylamino)pyridazin-3-yl]tetrazole The title compound was prepared from the appropriate cyano compound (reference example 17) using a similar method to that of example 12 except the mixture was heated at 85° C. for approximately 20 hours, monitoring the reaction by TLC. (80% yield).

NMR (200 MHz, DMSO-$d_6$) δ: 0.36 (m, 2H); 0.57 (m, 2H); 1.14–1.35 (m, 4H); 3.08 (s, 3H); 3.78 (q, 2H); 4.03 (d, J=6.2 Hz, 2H); 4.93 (s, 2H); 7.25 (d, J=8.3 Hz, 1H); 7.35 (d, J=8.3 Hz; 1H); 7.68 (d, J=2.1 Hz, 1H); 7.83 (dd, J=2.1, 8.3 Hz, 1H); 8.05 (d, J=8.3 Hz, 1H).

MS (ESP$^+$): 430 (M+H)$^+$.

EXAMPLE 17

5-[6-(N-[5-Bromo-2-propoxybenzyl]-N-ethylamino)pyridazin-3-yl]tetrazole

6-[N-(5-Bromo-2-propoxybenzyl)-N-ethylamino]-3-cyanopyridazine (reference example 18) (1.0 g, 2.67 mmol).

was dissolved in DMA (15 ml) and treated with sodium azide (520 mg, 8.0 mmol) followed by triethylammonium chloride (550 mg, 4.0 mmol) and the mixture heated at 110° C. for 3 hours. The solution was poured 2M hydrochloric acid (50 ml), extracted with ethyl acetate and dichloromethane (100 ml of each) and the combined extracts washed with water (3×100 ml), dried over $MgSO_4$ and concentrated in vacuo. Addition of ether and hexane precipitated a solid which was triturated with acetonitrile/toluene to give the title compound (965 mg, 87%).

MS (ESP+): 418 (M+H)$^+$, 390 (M+H–N$_2$)$^+$.

Elemental Analysis: $C_{17}H_{20}BrN_7O$. Calc: % C, 48.8; H, 4.82; N, 23.4 Found: % C, 49.1; H, 4.7; N, 23.5.

NMR (250 MHz, DMSO-d$_6$) δ: 0.99 (t, J=7 Hz, 3H); 1.17 (t, J=6 Hz, 3H); 1.72 (m, 2H); 3.72 (q, J=6 Hz, 2H); 4.0 (t, J=7 Hz, 2H); 4.82 (s, 2H); 6.98 (d, J=8.5 Hz, 1H); 7.22 (d, J=2 Hz, 1H); 7.27 (d, J=8 Hz, 1H); 7.40 (dd, J=2, 8 Hz, 1H); 8.03 (d, J=8.5 Hz, 1H).

EXAMPLE 18

6-(N-[5-Bromo-2-propoxybenzyl]-N-ethylamino) pyridazine-3-carboxylic Acid

6-[N-(5-Bromo-2-propoxybenzyl)-N-ethylamino]-3-cyanopyridazine (reference example 18) (1.5 g, 4 mmol) in ethanol (100 ml) was treated with aqueous sodium hydroxide (20 ml, 2M, 40 mmol) and was heated to 70° C. for 16 hours. The solvents were evaporated at reduced pressure, the residue dissolved in water, acidified with acetic acid and extracted with ethyl acetate (×4). The combined organic phases were washed with water and brine dried over $MgSO_4$ and concentrated in vacuo. The resulting gum was triturated with ether to give the title compound as a solid (1.24 g, 79%).

M.p. 135–137° C.

MS (ESP–): 392 (MH)$^-$,

Elemental Analysis: $C_{17}H_{20}BrN_7O$ Calc: % C, 51.8; H, 5.1; N, 10.7 Found: % C, 51.9; H, 5.3; N, 10.6.

EXAMPLE 19

N-Propyl-6-(N-[5-bromo-2-propoxybenzyl]-N-ethylamino)pyridazine-3-carboxamide 6-(N-[5-Bromo-2-propoxybenzyl]-N-ethylamino) pyridazine-3-carboxylic acid (example 18) (500 mg, 1.27 mmol) was dissolved in dichloromethane (50 ml), (1-(3-dimethylaminopropyl)-3-ethyl-carbodiimide hydrochloride (EDAC),(365 mg, 2.07 mmol), dimethylaminopyridine, (DMAP) (465 mg, 3.81 mmol) and propanesulfonamide (190 mg, 1.54 mmol) was added. The mixture was stirred at ambient temperature under argon overnight, after which TLC (5% methanol/dichloromethane) suggested the reaction was complete. The reaction mixture was loaded directly onto a MPLC column (silica) and the title compound obtained by elution 5% methanol/dichloromethane as a foam (380 mg, 60%).

MS(ESP+): 499 (M+H)$^+$.

Elemental Analysis: $C_{20}H_{27}BrN_4O_4S$ Calc: % C, 48.1; H, 5.45; N, 11.2. Found: % C, 48.2; H, 5.8; N, 10.8.

NMR (250 MHz, DMSO-d$_6$) δ: 0.95 (m, 6H), 1.17 (t, J=6 Hz, 3H); 1.7 (m, 2H); 3.37 (t, J=8 Hz, 2H); 3.67 (q, J=6 Hz, 2H); 3.95 (t, J=6 Hz, 2H); 4.82 (s, 2H); 6.98 (d, J=8.5 Hz, 1H); 7.12 (d, J=2 Hz, 1H); 7.17 (d, J=8 Hz, 1H); 7.37 (dd, J=2, 8 Hz, 1H); 7.83 (d, J=8.5 Hz, 1H).

EXAMPLE 20

N-(3,5-Dimethylisoxazo-4-ylsulphonyl)-6-(N-[5-bromo-2-propoxybenzyl]-N-ethylamino)pyridazine-3-carboxamide 6-(N-[5-Bromo-2-propoxybenzyl]-N-ethylamino) pyridazine-3-carboxylic acid (example 18) (500 mg, 1.27 mmol) was dissolved in dichloromethane (50 ml), (1-(3-dimethylaminopropyl)-3-ethyl-carbodiimide hydrochloride (EDAC), (365 mg, 2.07 mmol), dimethylaminopyridine. (DMAP) (465 mg, 3.81 mmol) and 3.5-dimethylisoxazoly-4-ylsulfonamide (270 mg, 1.53 mmol) was added. The mixture was stirred at ambient temperature under argon overnight. after which TLC (5%0 methanol/dichloromethane) suggested the reaction was complete. The reaction mixture was loaded directly onto a MPLC column (silica) and the title compound obtained by elution 5% methanol/dichloromethane as a gum which was further purified by trituration with ether to give the required product as a solid (180 mg, 33%).

M.p. 122–124° C.

MS(ESP+): 552 (M+H)$^+$.

Elemental Analysis: $C_{22}H_{26}BrN_5O_5S.1.1H_2O$ Calc: % C, 47.8; H, 4.7; N, 12.7. Found: % C, 46.2; H, 4.9; N, 12.2.

NMR (250 MHz, DMSO-d$_6$) δ: 0.95 (m, J=6 Hz, 3H), 1.12 (t, J=7 Hz, 3H); 1.72 (m, 2H); ); 2.27 (s, 3H); ); 2.55 (s, 3H); 3.62 (q, J=7 Hz, 2H); 3.95 (t, J=6 Hz, 2H); 4.72 (s, 2H); 6.93 (d, J=8.5 Hz, 1H); 6.97 (d, J=8 Hz, 1H); 7.17 (d, J=2 Hz, 1H); 7.37 (dd, J=2.8 Hz, 1H); 7.77 (d, J=8.5 Hz, 1H).

EXAMPLE 21

6-[N-(5-Chloro-2-(cyclopropylmethoxy)benzyl)-N-ethylamino]pyridazine-3-carboxamide A mixture of N-ethyl-5-chloro-2-(cyclopropylmethoxy) benzylamine (reference example 20) (4.4 g, 18.4 mmol), 6-chloropyridazine-3-carboxamide (3.0 g 19 mmol), di-isopropylethylamine (5.0 ml, 29 mmol) and DMF (25 ml) was stirred at reflux for 16 hours. The mixture was cooled and diluted with water (50 ml), the gum was allowed to settle out and the supernatant liquor decanted. The gum was dissolved in dichloromethane and stirred while adding 2N hydrochloric acid (50 ml). A precipitate formed after 10 minutes. The solid was filtered off and washed with dichloromethane (10 ml) and ether (20 ml) to give a buff solid (3.8 g, 61%) m.p. 177–8° C.

MS (ESP$^+$): 361/363 (M+H)$^+$).

NMR (200 MHz, DMSO-d$_6$) δ 0.34 (m, 2H), 0.57 (m, 2H), 1.16 (t, J=7 Hz, 3H), 1.25 (m, 1H), 3.70 (q, J=7 Hz, 2H), 3.78 (d, 2H), 4.81 (s, 2H), 7.00 (d, J=8 Hz, 1H), 7.05 (d, J=2 Hz, 1H), 7.17 (d, J=9 Hz, 1H), 7.25 (dd, J=2, 8 Hz, 1H), 7.45 (broad s, 1H), 7.85 (d, J=9 Hz, 1H). 8.07 (broad s, 1H).

EXAMPLE 22

6-[N-(5-Chloro-2-(cyclopropylmethoxy)benzyl)-N-ethylamino]pyridazine-3-carboxylic Acid The title compound was prepared as a white powder from 6-[N-(5-chloro-2-cyclopropylmethoxy)benzyl)-N-ethylamino]pyridazine-3-carboxamide (example 21) using similar method to that of example 26.

(Yield 86%).

m.p. 119–120° C.

MS (ESP$^+$): 362/364 (M+H)$^+$.

NMR (200 MHz, DMSO-d$_6$) δ 0.34 (m, 2H), 0.56 (m, 2H); 1.17 (t, J=7 Hz, 3H), 1.22 (m, 1H), 3.72 (q, J=7 Hz 2H) 3.90 (d, J=7 Hz, 2H), 4.83 (s, 2H), 7.02 (d, J 8 Hz,) 7.08 (d, J=2 Hz, 1H), 7.14 (d, J=9 Hz, 1H), 7.26 (dd, J=2, 8 Hz, 1H), 7.84 (d, J=9 Hz, 1H).

Elemental Analysis: Calculated % C, 59.8; H, 5.6; N, 11.6; Cl, 9.8. Found % C, 59.7; H, 5.6; N, 11.7; Cl, 9.9.

EXAMPLE 23

5-[6-(N-[5-Chloro-2-cyclopropylmethoxybenzyl]-N-ethylamino)pyridazin-3-yl]tetrazole The title compound was prepared from 6-[N-(5-chloro-2-cyclopropylmethoxybenzyl)-N-ethylamino]-3-cyanopyridazine (reference example 21) using a similar method to that of example 12.

(Yield 41%)

m.p. 190–192° C.

MS (ESP$^+$): 386/388 (M+H)$^+$.

NMR (200 MHz, DMSO-d$_6$) δ 0.35 (m, 2H), 0.57 (m, 2H), 1.20 (t, J=7 Hz, 3H), 3.77 (q, J=7 Hz, 2H), 3.90 (d, J=7 Hz, 2H), 4.85 (s, 2H), 7.01 (d, J=8 Hz, 1H), 7.14 (d, J=2 Hz, 1H), 7.25 (dd, J=2.8 Hz, 1H), 7.29 (d, J=8 Hz, 1H), 8.04 (d, J=8 Hz, 1H).

Analysis: Calc % C, 56.0; H, 5.2; N, 25.4. Found % C, 55.9; H, 5.3; N, 25.0.

EXAMPLE 24

N-Trifluoromethanesulphonyl-6-[N-(5-Chloro-2-cyclopropylmethoxybenzyl)-N-ethylamino] pyridazine-3-carboxamide The title compound was prepared from 6-[N-(5-chloro-2-cyclopropylmethoxybenzyl)-N-ethylamino]pyridazine-3-carboxylic acid (example 22) and trifluoromethanesulphonamide using a similar method to that of example 7. (Yield 18%). m.p. 150°-dec.

MS (ESP$^+$): 493/495 (M+H)$^+$.

NMR (200 MHz, DMSO-d$_6$) δ: 0.35 (m, 2H), 0.57 (m, 2H), 1.15 (t, J=7 Hz, 3H), 3.67 (q, J=7 Hz, 2H), 3.88 (d, J=7 Hz, 2H), 4.80 (s, 2H), 6.95–7.10 (m, 3H), 7.24 (dd, J=2, 8 Hz, 1H), 7.80 (d, J=8 Hz, 1H).

EXAMPLE 25

6-[N-(5-Chloro-2-cyclopentoxybenzyl)-N-ethylamine]pyridazin-3-carboxamide

N-Ethyl-5-chloro-2-cyclopentoxybenzylamine (reference example 22—used without further purification) (4.27 g, 16.8 mmol) in dimethylformamide (25 ml) was then treated with 6-chloropyridazin-3-carboxamide (described in reference example 3) (3.03 g, 19.2 mmol) and ethyl diisopropylamine (5 ml, 29 mmol) and left to reflux at 140° C. for 16 hours. Water (50 ml) was added and the product extracted into dichloromethane and ether, dried over anhydrous magnesium sulfate, filtered and purified by column chromatography (2% propan-2-ol in dichloromethane) to give 1.44 g of yellow gum. Trituration with ether yielded the title compound (790 mg, 13%).

MS (ESP+); 375/377 (MH+).

NMR (200 MHz, DMSO-d$_6$) δ: 1.08 (t, 31H), 1.60 (m, 6H); 1.87 (mn, 2H); 3.62 (q, 2H); 4.74 (s, 2H), 4.85 (m, 1H); 7.03 (m, 2H); 7.13 (d, 1H); 7.24 (dd, 1H); 7.42 (br s, 1H); 7.82 (d, 1H); 8.08 (br s, 1H).

EXAMPLE 26

6-[N-(5-Chloro-2-cyclopentoxybenzyl)-N-ethylamine]pyridazin-3-carboxylic Acid

6-[N-(5-Chloro-2-cyclopentoxybenzyl)-N-ethylamine] pyridazin-3-carboxamide (example 25) (0.75 g, 2.0 mmol) was dissolved in ethanol (50 ml), 2N sodium hydroxide (15 ml) added and the solution left to reflux at 80° C. for 16 hours. Once cool, the solvent was removed in vacuo and water (100 ml) added. The solution was acidified with glacial acetic acid and the title compound extracted into dichloromethane, washed with water (2×100 ml) and dried over anhydrous magnesium sulfate. The solvent was evaporated and the product recrystallised from dichloromethane, ether and hexane upon standing. (100 mg, 13%)

MS (ESP+): 376 378 (MH+).

NMR (200 MHz, DMSO-d$_6$, 373K) δ: 0.79 (t, 3H); 1.62 (m, 6H); 1.88 (m, 2H); 3.15 (m, 2H); 4.38 (s, 2H); 4.80 (m, 1H); 6.80 (br s, 1H); 6.95 (d, 1H); 7.22 (dd, 1H); 7.32 (d, 1H); 7.93 (d, 1H).

EXAMPLE 27

5-[6-(N-[5-Chloro-2-cyclopentoxybenzyl]-N-ethylamino)pyridazin-3-yl]tetrazole

The title compound was prepared from 6-(N-[5-Chloro-2-cyclopentoxybenzyl]-N-ethylamino)-3-cyanopyridazine (reference example 23) using a similar method to that of example 12 except the reaction was stirred at 150° C. for 9 hours, the solution was acidified with 1N hydrochloric acid and the product was extracted into dichloromethane (2×100 ml) and purified by column chromatography (10% propan-2-ol, 0.1% methanoic acid in dichloromethane). Ether trituration gave the title product (225 mg, 18%).

MS (ESP+): 400/402 (MH+).

NMR (200 MHz, DMSO-d$_6$) δ: 1.14 (t, 3H); 1.60 (m, 4H); 1.70 (m, 2H); 1.88 (m, 2H); 3.65 (q, 2H); 4.78 (s, 2H); 4.87 (m, 1H); 7.02 (d, 1H), 7.13 (d, 1H); 7.28 (m, 2H); 8.03 (d, 1H).

EXAMPLE 28

N-(3,5-Dimethylisoxazol-4-ylsulphonyl)-6-[N-(5-bromo-2-(2-methylpropoxy)benzyl)-N-ethylamino] pyridazine-3-carboxamide The title compound was prepared from 6-[5-bromo-2-(2-methylpropoxy)benzyl)-N-ethylamino]pyridine-3-carboxylic acid (example 9) and 3,5-dimethylisoxazol-4-ylsulphonamide using a similar method to that of example 14.

NMR(200 Hz, DMSO-d$_6$) δ 0.98 (d, 6H), 1.15(t, 3H); 1.95–2.06 (m, 1H); 2.38(s, 3H); 2.7 (s, 3H); 3.69 (q, 2H); 3.8 (d, 2H); 4.85 (s, 2H); 6.98 (d, 1H); 7.13 (d, 1H); 7.2 (d, 1H); 7.39 (dd, 1H); 7.8 (d 1H).

EXAMPLE 29

6-[N-(5-Methanesulphonyl-2-(cyclopropylmethoxy)benzyl)-N-ethylamino]pyridazine-3-carboxylic Acid 6-[N-(5-Methanesulphonyl-2-(cyclopropyloxy)benzyl)-N-ethylamino]-3-cyanopyridazine (900 mg, 2.3 mmol) in ethanol (30 ml) and water (6 ml) was treated with sodium hydroxide pellets (0.93 g, 23 mmol) and the resultant solution heated at 80° C. overnight (the reaction was monitored by HPLC). The mixture was then evaporated to low volume, water was added and the mixture extracted with ethyl acetate (×3) (a small quantity of insoluble material was ignored). The aqueous layer was acidified with acetic acid and extracted with ethyl acetate. The combined organic extracts were washed with brine, dried and evaporated to leave a gum. The gum was dissolved in dichloromethane and evaporated to give the title compound as a foam (0.56 g, 60%) MS (ESP$^-$): 404 (M–H$^-$).

NMR (200 MHz, DMSO-d$_6$) δ 0.3–0.4 (m, 2H); 0.52–0.6 (m, 2H); 1.1–1.3 (m +t, 4H); 3.05 (s, 3H); 3.72 (q, 2H); 4.0 (d, 2H); 4.87 (s, 2H); 7.18 (d, 1H); 7.24 (d, 1H); 7.58 (d, 1H); 7.8 (dd, 1H); 7.84 (d, 1H).

EXAMPLE 30

N-(Propanesulphonyl)-6-[N-(5-methanesulphonyl-2-(cyclopropylmethoxy)benzyl)-N-ethylamino]pyridazine-3-carboxamide The title compound was prepared from 6-[N-(5-methanesulphonyl-2-(cyclopropylmethoxy)benzyl)N-ethylamino]pyridazine-3-carboxylic acid (example 29) using a similar method to that of example 14.

MS (ESP$^+$): 511.2 (M+H)$^+$.

NMR (200 MHz, DMSO-d$_6$) δ: 0.29–0.38 (m, 2H); 0.5–0.62 (m, 2H); 0.98 (t, 3H); 1.3–1.1 (m+t, 4H); 1.65–1.82 (m, 2H); 3.05 (s, 3H); 3.43 (t, 2H); 3.75 (q, 2H); 4.0 (d, 2H); 4.9 (s, 2H); 7.23 (d, 1H); 7.27 (d, 1H); 7.56 (d, 1H); 7.8 (dd, 1H); 7.85(d, 1H).

EXAMPLE 31

N-Propanesulphonyl-6-[N-(5-bromo-2-(2-methylpropoxy)benzyl)-N-ethylamino]pyridazine-3-carboxamide The title compound was prepared from the corresponding acid (example 9) using a method similar to that of example 7.

NMR (250 MHz DMSO-d$_6$)δ: 1.00 (m, 9H); 1.15 (t, 3H); 1.75 (m, 2H); 2.03 (m, 1H); 3.45(m, 2H); 3.70 (q, 2H); 3.80 (d, 2H); 4.86 (s, 2H); 7.0 (d, 1H), 7.13 (d, 1H); 7.21 (d, 1H); 7.40 (dd, 1H); 7.87 (d, 1H).

EXAMPLE 32

N-(3,5-Dimethylisozazol-4-ylsulphonyl)-6-[N-(5-bromo-2-(3,3,3-trifluoro-2-hydroxypropoxy)benzyl)-N-ethylamino]pyridazine-3-carboxamide The title compound was prepared from 6-[N-(5-bromo-2-(3,3,3-trifluoro-2-hydroxypropoxy)benzyl)-N-ethylamino]pyridazine-3-carboxylic acid (example 15) using a similar method to that of example 7.

NMR (250 MHz,DMSO-d$_6$) δ: 1.15(t, 3H); 2.35(s, 3H); 2.63 (s, 3H); 3.68 (q, 2H); 4.2 (m, 2H); 4.40(m, 1H); 4.82(s, 2H); 6.65(d, 1H); 7.05(m, 2H); 7.2(m, 1H); 7.40 (dd, 1H); 7.80 (d, 1H);

MS (ESP+) 622 (M+H)$^+$.

EXAMPLE 33

6-[N-(5-Bromo-2-(cyclobutyloxy)benzyl)-N-ethylamino]pyridazine-3-carboxylic Acid The title compound was prepared from the corresponding nitrile (reference example 24) using a similar method to that of example 29.

MS (ESP$^+$): 406 (M+H)$^+$.

NMR (250 MHz DMSO-d$_6$) δ 1.15(t, 3H); 1.73 (m, 2H); 2.00 (m, 2H); 2.42(m, 2H); 3.69(q, 2H); 4.72 (quintet, 1H); 4.81 (s, 2H); 6.82 (d, 1H); 7.12 (d, 1H); 7.16 (d, 1H); 7.36 (dd, 1H); 7.83 (d, 1H).

EXAMPLE 34

5-[6-(N-[5-bromo-2-(3-3,3-trifluoro-2-hydroxypropoxy)benzyl]-N-ethylamino)pyridazin-3-yl]tetrazole The title compound was prepared from the corresponding nitrile (reference example 25) by a similar method to that of example 12.

MS (ESP)$^+$: 488 (M+H)$^+$.

NMR (250 MHz DMSO-d$_6$) δ: 1.18(t,3H); 3.72(q,2H); 4.16 (m, 1H); 4.27 (m, 1H); 4.44 (m, 1H) 4.84 (s, 2H); 6.66 (bd, 1H); 7.08 (d, 1H); 7.19 (d, 1H); 7.25 (d, 1H); 7.41 (dd, 1H); 8.03 (d, 1H).

EXAMPLE 35

2-[N-(5-Bromo-2-cyclopropylmethoxybenzyl)-N-ethylamino]pyridine-5-carboxylic Acid 2-[N-(5-Bromo-2-cyclopropylmethoxybenzyl)-N-ethylamino]-5-cyanopyridine (reference example 26) (7.5 g, 19.43 mmol) was dissolved in ethanol (400 ml) and sodium hydroxide (7.8 g, 174 mmol) and then water (80 ml) added. The mixture was heated at reflux for 16 hours, the ethanol removed in vacuo, and the residue extracted with ethyl acetate (4×100 ml). The organic extracts were acidified with acetic acid and washed with water (100 ml) to give a solid (6.8 g). This solid was dissolved in n-butanol (400 ml) and sodium hydroxide (6.75 g, 169 mmol) and water (80 ml) was added. The mixture was heated at reflux for 72 hours, the butanol removed in vacuo, water (100 ml) added and the residue extracted with ethyl acetate(4×100 ml). The organic extracts were acidified with acetic acid and washed with water (100 ml). The combined aqueous layers were then acidified and extracted with ethyl acetate (4×100 ml) to give the title product as a solid (2.4 g, 30%). M.p. 175–177° C.

MS: 404 (M–H)$^-$.

NMR (MHz, DMSO-d$_6$) δ: 0.30(m, 2H); 0.55 (m, 2H); 1.12(m, 4H); 3.55 (q, 2H); 3.85 (d, 2H); 4.68 (s, 2H); 6.62(d, 1H); 6.92 (d, 1H); 7.05 (d, 1H); 7.35 (dd, 1H); 7.88 (dd, 1H); 8.58 (d, 1H)12.30(s, 1H).

Elemental Analysis: C$_{19}$H$_{21}$BrN$_2$O$_3$. Calc: % C, 56.3; H, 5.2; N, 6.9 Found: % C, 56.1; H, 5.3; N, 6.8.

EXAMPLE 36

6-[N-(5-Chloro-2-cyclobutylmethoxybenzyl)-N-ethylamino]pyridazine-3-carboxylic Acid The title compound was prepared from using a similar method to that of example 18 by treating 6-[N-(5-Chloro-2-cyclobutylmethoxybenzyl)-N-ethylamino]-3-cyanopyridazine (reference example 27) (2.3 g, 6.46 mmol) with sodium hydroxide (2.6 g, 65 mmol) in water (20 ml) and ethanol (100 ml) to give a gum which solidified on trituration with ether (1.15 g, 47%).

M.p. 140–142° C.

MS: 374 (M–H)$^-$.

NMR (MHz, DMSO-d$_6$) δ: 1.1(t, 3H); 1.95 (m, 6H); 2.70(m, 1H); 3.68 (q, 2H); 4.0 (d, 2H); 4.8 (s, 2H); 7.0(m, 3H); 7.25(dd, 1H); 7.82 (d, 1H).

Elemental Analysis: C$_{19}$H$_{22}$ClN$_3$O$_3$. Calc: % C, 60.5; H, 5.9; N, 11.2 Found: % C, 60.5; H, 6.0; N, 10.9.

EXAMPLE 37

6-[N-(5-Bromo-2-cyclopropylmethoxybenzyl)-N-propylamine]pyridazine-3-carboxylic Acid The title compound was made from the corresponding ester [which was prepared >using similar methods to those described in reference example 3, using propylamine in place of ethylamine, and reference example 4] using a similar method to that of example 1 (20%).

MS (ESP+) 420/422 (MH+).

NMR (200 MHz, DMSO-d$_6$) δ: 0.25 (m, 2H), 0.57 (m, 2H); 0.91 (t, 3H); 1.21 (m, 1H); 1.61 (m, 2H); 3.63 (t, 2H); 3.88 (d, 2H); 4.83 (s, 2H); 6.96 (d, J=8 Hz, 1H); 7.13 (d, J=9 Hz, 1H), 7.16 (d, J=2 Hz, 1H); 7.38 (dd, J=2 Hz, 8 Hz, 1H); 7.82 (d, J=9 Hz 1H).

EXAMPLE 38

N-(3,5-Dimethylisoxazol-4-ylsulphonyl)-6-[N-(5-Bromo-2-cyclopropylmethoxybenzyl)-N-propylamine]pyridazine-3-carboxamide The title compound was prepared from 6-[N-(5-Bromo-2-cyclopropylmethoxybenzyl)-N-ethylamine]pyridazine-3-carboxylic acid (example 37) using a similar method to that of example 7, except that dichloromethane was used as the solvent and no column purification was neccessary. Recrystallisation (diethyl ether/hexane) gave the title compound (340 mg, 49%).

MS(ESP+): 578/580(MH+).

NMR (250 MHz, DMSO-d$_6$) δ: 0.33 (m, 2H); 0.54 (m, 2H); 0.88 (t, 3H); 1.19 (m, 2H); 1.60 (mn, 2H); 2.40 (s, 3H) 2.68 (s, 3H); 3.60 (t, 2H); 3.87 (d, 2H); 4.84 (s, 2H); 6.96 (d, J=8 Hz, 1H), 7,17 (d, J—2 Hz, 1H); 7.23 (d, J=9 Hz, 1H); 7.38 (dd, J=2 Hz,8 Hz, 1H); 7.81 (d, J=9 Hz, 1H),

EXAMPLE 39

6-[N-(5-Bromo-2-cyclopropylmethoxybenzyl)-N-methylamino]pyridazine-3-carboxylic Acid The title compound was prepared using a similar method to that of example 37 from the appropriate N-methyl compound.

MS (ESP+): 392/394 (MH+).

NMR (250 MHz, DMSO-d$_6$) δ: 0.33 (m, 2H); 0.55 (m, 2H), 1.19 (m, 1H); 3.38 (d, 2H); 4.86 (s, 2H); 6.97 (d, J=8 Hz, 1H); 7.17 (d, J=10 Hz, 1H); 7.20 (d, J=2 Hz, 1H); 7.37 (dd, J=8 Hz, 2 Hz, 1H); 7.84 (d=J=10 Hz).

EXAMPLE 40

N-(3,5-Dimethylisoxazol-4-ylsulphonyl )-6-[N-(5-bromo-2-cyclopropylmethoxybenzyl)-N-methylamino]pyridazine-3-carboxamide The title compound was prepared using a similar method to that of example 38 from the corresponding carboxylic acid.

MS (ESP+); 550/552 (MH+).

NMR (250 MHz, DMSO-d$_6$) δ: 0.30 (m, 2H); 0.52 (m, 2H); 1.16 (m, 1H); 2.39 (s, 3H); 2.69 (s, 3H); 3.22 (s, 3H); 3.85 (d, 2H); 5.87 (s, 2H); 6.95 (d, J=8 Hz, 1H); 7.20 (d, J=2 Hz, 1H); 7.27 (d, 1H); 7.39 (dd, J=2 Hz, 8 Hz, 1H); 7.84 (d, 1H).

REFERENCE EXAMPLE 1

Methyl 2-[N-(5-bromo-2-propoxybenzyl)-N-ethylamino]pyridine-5-carboxylate

6-Chloronicotinic acid (100 g, 0.63 mol) was treated with ethylamine (70% in water, 500 ml). The reaction was sealed in an autoclave and heated to 170° C. for 6 hours. The reaction mixture was evaporated, partially neutralised with concentrated HCl and the pH adjusted to pH 5 with glacial acetic acid. The solid product was filtered off and dried in vacuo for 18 hours to give 6-(ethylamino)nicotinic acid (87.8 g, 84%).

MS (CI$^+$)=167 (M+H)$^+$.

NMR (250 MHz, DMSO-d$_6$) δ: 1.15 (t, J=7 Hz, 3H); 3.3 (q, J=7 Hz, 2H); 6.45 (d, J=9 Hz, 1H); 7.25 (brt, 1H); 7.78 (dd, J=2, 9 Hz, 1H); 8.54 (d, J=2 Hz, 1H); 11.6 (brs, 1H).

A suspension of 6-(ethylamino)nicotinic acid (50 g, 0.3 mol) in methanol (500 ml) was treated with concentrated H$_2$SO$_4$ (30 ml). The reaction was heated at reflux for 18 hours. The reaction mixture was then evaporated, poured into ice water (1 L) and adjusted to pH 8 with solid sodium hydrogen carbonate (foaming). The aqueous mixture was extracted with ethyl acetate (3×300 ml) and the organic layers combined, dried (MgSO$_4$) and evaporated to give methyl 6-(ethylamino)nicotinoate as an off-white solid (45.5 g, 84%).

NMR (200 MHz, DMSO-d$_6$) δ: 1.14 (t, J=7 Hz, 3H); 3.3 (q, J=7 Hz, 2H), 3.76 (s, 3H); 6.46 (d, J=9 Hz, 1H); 7.39 (brt, 1H); 7.80 (dd, J=3, 9 Hz, 1H); 8.56 (d, J=3 Hz, 1H).

A solution of 5-bromosalicylaldehyde (12.0 g, 59.7 mmol) in DMF (50 ml) was treated with K$_2$CO$_3$ (16.5 g, 120 mmol) and benzyl bromide (11.2 g, 65.6 mmol). The reaction was stirred at ambient temperature for 18 hours. diluted with ethyl acetate and filtered. The filtrate was washed with HCl (0.05 M), saturated aqueous sodium hydrogen carbonate and brine. The organic phase was dried (Na$_2$SO$_4$) and evaporated and the residue triturated with hexane/ethyl ether. The product was filtered off to give 2-benzyloxy-5-bromobenzaldehyde as a white solid (15.8 g, 90%) m.p. 70–72° C.

MS (CI+): 291 (M+H)$^+$.

NMR (200 MHz, DMSO-d$_6$) δ: 5.38 (s, 2H); 7.5 (m, 6H); 7.9 (m, 2H); 10.41 (s, 1H).

A suspension of 2-benzyloxy-5-bromobenzaldehyde (14.5 g, 50.2 mmol) in absolute ethanol (250 ml) was treated with sodium borohydride (2.6 g, 68.8 mmol). The reaction was stirred and the temperature slowly rose to 33° C. After 1 hour the reaction mixture was evaporated and the residue dissolved in ethyl acetate and poured into a mixture of ice water (200 ml) and 1 N HCl (25 ml). The organic layer was separated, washed with aqueous sodium hydrogen carbonate, brine, dried (Na$_2$SO$_4$) and evaporated to give 2-benzyloxy-5-bromobenzylalcohol as a pale yellow oil (14.85 g, quantitative).

MS (CI+) 292 (M+).

NMR (200 MHz, DMSO-d$_6$) δ: 4.52 (d, J=5 Hz, 2H); 5.12 (s, 2H); 5.17 (t, J=5 Hz, 1H); 6.98 (d, J=9 Hz, 1H); 7.4 (m, 6H); 7.5 (d, 2H, 1H).

A solution of 2-benzyloxy-5-bromobenzyl alcohol (14.75 g, 50.2 mmol) in anhydrous ethyl ether (150 ml) was cooled to 4° C. A solution of PBr$_3$ (13.68 g, 50 mmol) in anhydrous ether (40 ml) was added dropwise keeping the temperature below 10° C. The reaction was allowed to warm to ambient temperature and stirred for 1 hour. The reaction was filtered through silica gel (200 g). The silica gel was washed with ethyl ether to remove all the product. The filtrate was washed with water (1×150 ml), aqueous saturated sodium hydrogen carbonate (1×150 ml) and brine (1×150 ml). The organic layer was dried (Na$_2$SO$_4$) and evaporated to give 2-benzyloxy-5-bromobenzylbromide as a pale yellow oil (15.2 g, 85%) which crystallised on standing.

MS (EI+): 354 (M+).

NMR (200 MHz, DMSO-d$_6$); δ: 4.65 (s, 2H); 5.2 (s 2H); 7.05 (d, J=9 Hz, 1H), 7.4 (m, 6H); 7.66 (d, J=3 Hz, 1H).

A solution of methyl 6-ethylaminonicotinoate (15.2 g, 84.4 mmol) in DMF (50 ml) was cooled to 0° C. and treated with sodium hydride (60%. 75 mmol). The reaction was stirred for 1 hour and a solution of 2-benzyloxy-5-bromobenzylbromide (25 g 70.2 mmol) in DMF (50 ml) added. The reaction was allowed to warm to ambient temperature and stirred for 18 hours. The reaction was quenched with water and extracted with ethyl acetate (three times). The organic layers were combined, washed with water and brine twice, dried (MgSO$_4$) and evaporated to give a white solid. Recrystallisation from ethyl acetate/hexane gave methyl 2-[N-(2-benzyloxy-5-bromobenzyl)-N-ethylamino] pyridine-5-carboxylate (22.7 g, 71%).

MS (CI+): 455/457 (M+H)$^+$.

NMR (200 MHz, DMSO-d$_6$) δ: 1.1 (t, J=7 Hz, 3H); 3.5 (q, J=7 Hz, 2H); 3.78 (s, 3H); 4.77 (s, 2H); 5.18 (s, 2H); 6.65 (d, J=9 Hz, 1H); 7.08 (m, 2H); 7.4 (m, 6H); 7.9 (dd, J=2, 9 Hz, 1H); 8.62 (d, 1H).

A solution of methyl 2-[N-(2-benzyloxy-5-bromobenzyl)-N-ethyl-amino]pyridine-5-carboxylate (10.0 g, 22 mmol) in dichloromethane (950 ml) was treated with boron trichloride dimethyl sulphide complex (40 ml, 2M, 80 mmol). The reaction was stirred at ambient temperature for 48 hours. Saturated aqueous sodium hydrogen carbonate solution was added and the layers were washed with dichloromethane. The organic layers were combined. dried (MgSO$_4$) and evaporated to give an off white solid which was subjected to chromatography (eluant: ethyl acetate/hexane) to give methyl 2-[N-(5-bromo-2-hydroxybenzyl)-N-ethylamino] pyridine-5-carboxylate (6.02 g, 75%).

MS (CI$^+$): 365 (M+H)$^+$.

NMR (250 MHz, DMSO-d$_6$): δ 1.14 (t, J=7 Hz, 3H); 3.61 (q, J=7 Hz, 2H); 3.78 (s 3H); 4.66 (s, 2H); 6.65 (d, J=9 Hz, 1H); 6.8 (d, J=9 Hz, 1H); 7.02 (d, J=2 Hz, 1H); 7.2 (dd, J=2, 9 Hz, 1H); 7.93 (dd, J=2. 9 Hz, 1H); 8.64 (d, J=2 Hz, 1H); 10.13 (s, 1H).

1-Bromopropane (0.12 g, 0.69 mmol) was treated with a solution of methyl 2-[N-(5-bromo-2-hydroxybenzyl)-N-ethylamino]-5-pyridylcarboxylate (0.2 g, 0.55 mmol) in DMF (4 ml). Potassium carbonate (230 mg, 1.7 mmol) was added to this solution and the reaction mixture was stirred for 18 hours. The solvent was evaporated and the residue taken up in water (4 ml) and extracted with ethyl acetate (3×3 ml). The combined extracts were evaporated and the residue subjected to chromatography (eluant: ethyl acetate/hexane) to give the title compound as a pale yellow oil (0.122 g, 54%) which was used in the subsequent step without further purification.

REFERENCE EXAMPLE 2

Methyl 2-[N-(5-bromo-2-(2-methylpropoxy)benzyl)-N-ethylamino]-pyridine-5-carboxylate A solution of the methyl-2-[N-(5-bromo-2-(hydroxybenzyl)-N-ethylamino]pyridine-5-carboxylate (reference example 1, paragraph 7) (0.5 g, 1.37 mmol) in THF (15 ml) was treated with triphenylphosphine (0.39 g, 1.49 mmol) and diazoethyldicarboxylate. The reaction was stirred at ambient temperature for five minutes and then isobutyl alcohol (0.152, 2.06 mmol,) added. The reaction was then stirred at ambient temperature for 18 hours. partitioned between ethyl acetate and water and the aqueous layer washed with ethyl acetate (×2). The organic layers were combined, washed with water and brine, dried (MgSO$_4$) and evaporated. The residue was subjected to chromatography (eluant: ethyl acetate/hexane) to give the title compound (0.35 g, 60%) as an off-white solid.

MS (Cl$^+$): 421 (M+H)$^+$.

NMR (250 MHz, DMSO-d$_6$) δ: 1.0 (d, J=6 Hz, 3H); 1.12 (t, J=7 Hz, 6H); 2.04 (m, 1H); 3.6 (q, J=7 Hz, 2H); 3.78 (s, 3H); 3.80 (s, 2H); 4.75 (s, 2H); 6.66 (d, J=9 Hz, 1H); 6.97 (d, J=9 Hz, 1H); 7.05 (d, J=2 Hz, 1H); 7.37 (dd, J=2, 9 Hz, 1H); 7.93 (dd, J=2, 9 Hz, 1H); 8.73 (d, J=2 Hz, 1H).

REFERENCE EXAMPLE 3

Butyl 6-[N-(5-bromo-2-hydroxybenzyl)-N-ethylamino]-pyridazine-3-carboxylate

A solution of 6-oxo-1,6-dihydropyridazine-3-carboxylic acid (British patent no. 856409) (52 g, 0.33 mol) in nBuOAc (80 ml) and butanol (80 ml) was treated with concentrated sulphuric acid (5 ml). The mixture was heated at reflux under a Dean-Stark trap. After 5 hours water production had ceased. The reaction was allowed to cool to ambient temperature and after standing overnight, the precipitate was filtered, washed with diethyl ether and dried to give butyl 6-oxo-1,6-dihydropyridazine-3-carboxylate as a white solid (55.2 g, 85%) m.p. 81–83° C.

A solution of the above butyl ester (55.2 g, 0.28 mol) in acetonitrile (220 ml) was added carefully to POCl$_3$ (55.2 ml, 0.60 mol). The resultant solution was stirred at 100° C. for 2 hours. The reaction was cooled, evaporated at reduced pressure. The residue was dissolved in dichloromethane (280 ml) and added to a cold stirred solution of sodium carbonate (55 g) in water (280 ml). The mixture was stirred until all effervescence ceased, then the layers were separated and the organic layers dried (MgSO$_4$) and filtered through a pad of silica gel. The solution was evaporated to give butyl 6-chloropyridazine-3-carboxylate as a pale pink solid (51 g, 85%).

A solution of the chloro pyridazine compound from the previous step (51 g, 0.238 mole) in THF (375 ml) was treated with methanolic ammonia (saturated, 80 ml). The reaction was allowed to stand at ambient temperature overnight. The precipitate was filtered and dried to give 6-chloropyridazine-3-carboxamide as a pink solid (18.2 g, 49%). [Further material could be obtained by evaporating the filtrate (at reduced pressure) and treating the residue with THF (100 ml) and methanolic ammonia (40 ml). The product was isolated as before to give a pink solid (17.4 g). Total yield (35.6 g, 95%)].

A suspension of 6-chloropyridazine-3-carboxamide (28.5 g, 0.18 mol) in methanol (200 ml) was treated with aqueous ethylamine (70% solution, 77 ml). The reaction was heated at reflux for 3½ hours. The reaction was allowed to cool to ambient temperature and stand overnight. The precipitate was filtered and washed with a small volume of water and dried to give 6-(ethylamino)pyridazine-3-carboxamide as pink solid (8.9 g). [The filtrates were evaporated to a small volume diluted with cold water (100 ml) and more of the desired solid was filtered-off, washed with water and dried (12.8 g). Total yield (21.7 g, 72%)].

A solution of 6-(ethylamino)pyridazine-3-carboxamide (21.7 g, 0.131 mol) in n-butanol (109 ml) and BF$_3$.Et$_2$O (54 ml) was heated under an air condenser (allowing evaporation of Et$_2$O) at 120° C. for 18 hours. The reaction was evaporated at reduced pressure and the residue dissolved in ice/water (400 ml) and neutralized with stirring using solid sodium bicarbonate. The oily precipitate was extracted with dichloromethane (250 ml) containing methanol (50 ml). The extracts were dried (MgSO$_4$) and evaporated (in vacuo) to give a slightly sticky solid which was recrystallized from ethyl acetate (~250 ml) to give butyl 6-(ethylamino) pyridazine-3-carboxylate as an off-white solid (22.0 g, 75%).

A suspension of the butyl ester from the previous step (21 g, 0.094 mol) in acetic acid (400 ml) was treated with 4-bromophenol (65.5 g, 0.378 mol) and paraformaldehyde (3.15 g, 0.1 05 mol). The reaction was heated at 100° C. for 4.5 hours and a further portion of paraformaldehyde (6.3 g, 0.21 mol) added and the reaction heated at 100° C. for 16 hours. The resulting dark coloured reaction was evaporated to give a dark oil. Chromatography (eluant: diethyl ether/hexane) gave fast running materials as a brown oil. This oil was dissolved in ethyl acetate (~70 ml) and allowed to stand overnight at ambient temperature to give a white solid precipitate, which was filtered and washed with ethyl acetate and dried to give butyl 6-[N-(5-bromo-2-hydroxybenzyl)-N-ethylamino]pyridazine-3- carboxylate as the product (12.3 g, 32%).

REFERENCE EXAMPLE 4

Butyl 6-[N-(5-bromo-2-cyclopropylmethoxybenzyl)-N-ethylamino]pyridazine-3-carboxylate A solution of n-butyl 6-[N-(5-bromo-2-hydroxybenzyl)-N-ethylamino]pyridazine-3-carboxylate (reference example 3) (0.286 g, 0.69 mmol) in DMF (3.5 ml) was treated with bromomethylcyclopropane (0.1 g, 0.78 mmol) and potassium carbonate (0.473 g, 3.4 mmol). The reaction was allowed to stir at ambient temperature for 60 hours. The solvent was evaporated at reduced pressure (vacuum pump) and the residue partitioned between ethyl acetate and water. The aqueous layer was extracted with ethyl acetate (2×10 ml). The organic layers were combined dried (MgSO$_4$) and evaporated. The residue was purified by chromatography (eluant ethyl acetate/hexane) to give the title compound as a pale yellow oil (0.3 g, 94%).

MS (ESP+): 462 (M+H)$^+$.

NMR (200 MHz, DMSO-d$_6$) δ: 0.32 (m, 2H); 0.55 (m, 2H); 0.93 (t, J=7 Hz, 3H); 1.15 (m, 4H); 1.42 (m, 2H); 1.7 (m, 2H); 3.7 (q, J=7 Hz, 2H); 3.89 (d, J=7 Hz, 2H); 4.3 (t, J=7H, 2H); 4.84 (s, 2H); 6.98 (d, J=8 Hz, 1H); 7.15 (m, 2H); 7.4 (dd, J=3.9 Hz); 7.82 (d, J=8 Hz, 1H).

REFERENCE EXAMPLE 5

Methyl 2-[N-(5-bromo-2-(cyclopentylmethoxy)benzyl)-N-ethylamino]pyridine-5-carboxylate The title compound was prepared using a similar method to that of reference example 2 (from the phenol in reference example 1, paragraph 7) using cyclopentylmethanol in place of isobutyl alcohol to give a yield of 60%.

MS (ESP+): (M+H)$^-$447

NMR (200 MHz, DMSO-d$_6$) δ: 1.11 (t, J=7 Hz, 3H); 1.35 (m, 2H); 1.58 (m, 4H); 1.77 (m, 2H); 2.3 (m, 1H); 3.6 (q, J=7 Hz, 2H); 3.79 (s, 3H); 3.9 (d, J=7 Hz, 2H); 4.75 (s, 2H); 6.68 (d, J=9 Hz, 1H); 6.8 (d, J=9 Hz, 1H); 7.07 (d, J=2 Hz, 1H); 7.38 (dd, J=2. 9 Hz, 1H); 7.94 (dd, J=2. 9 Hz, 1H); 8.65 (d, J=2H, 1H).

REFERENCE EXAMPLE 6

Butyl 6-[N-(5-bromo-2-propoxybenzyl)-N-ethylamino]pyridazine-3-carboxylate

The title compound was prepared by reacting 1-iodopropane and butyl 6-[N-(5-bromo-2-hydroxybenzyl)-N-ethylamino]pyridazine-3-carboxylate (reference example 3) using a similar method to that of reference example 4.

MS (ESP$^+$): 450/452 (M+H$^+$).

REFERENCE EXAMPLE 7

Butyl 6-[N-(5-bromo-2-butoxybenzyl)-N-ethylamino]pyridazine-3-carboxylate

The title compound was prepared by reacting 1-iodobutane and butyl 6-[N-(5-bromo-2-hydroxybenzyl)-N-ethylamino]pyridazine-3-carboxylate using a similar method to that of reference example 4.

MS (ESP$^+$): 464/466 (M+H)$^+$.

REFERENCE EXAMPLE 8

6-[-(5-Bromo-2-hydroxybenzyl)-N-ethylamino]pyridazine-3-carboxylic Acid

A solution of butyl 6-[N-(5-bromo-2-hydroxybenzyl)-N-ethylamino]pyridazine-3- carboxylate (reference example 3) (0.36 g, 1.0 mmol) in THF (4 ml) and methanol (4 ml) was treated with aqueous sodium hydroxide 1N (4 ml) and allowed to stand at ambient temperature for 1.5 hours. The reaction was evaporated to a small volume, diluted with water and acidified with acetic acid. After standing for 18 hours, the precipitate was filtered, washed with water and ether, and dried (MgSO$_4$) to give the title compound as a white solid (0.26 g, 71%).

MS: (ESP+) 352/354 (M+H)$^+$.

NMR (200 MHz, DMSO-d$_6$) δ: 1.15 (t, J=6.67 Hz, 3H); 3.68 (q, J=6.67 Hz, 2H); 4.75 (s, 2H); 6.83 (d, J=8.34 Hz, 1H); 7.10 (d, J=8.34 Hz, 1H); 7.13(d, J=2.33 Hz, 1H); 7.25 (dd, J=10.00, 2.33 Hz, 1H); 7.83 (d, J=10.00 Hz, 1H).

REFERENCE EXAMPLE 9

2-[N-(5-Bromo-2-hydroxybenzyl)-N-ethylamino]pyridine-5-carboxylic Acid

A solution of methyl 2-[N-(5-bromo-2-hydroxybenzyl)-N-ethylamino]pyridine-5-carboxylate (see reference example 1) (10.2 g, 0.55 mmol) in THF (3 ml) and methanol (5 ml) was treated with 1N aqueous sodium hydroxide solution (2.7 ml) and was heated to 40° C. for 24 hours. The solvents were evaporated at reduced pressure, the residue treated with 1N acetic acid (2.7 ml) and the precipitate filtered, washed with water and air dried to give the title compound (0.17 g, 92%).

MS (FAB+): 351 (M+H)$^+$.

NMR (200 MHz, DMSO-d$_6$) δ: 1.12 (t, J=7 Hz, 3H); 3.6 (q, J=7 Hz, 2H); 4.64 (s, 2H); 6.6 (d, J=9 Hz, 1H); 6.83 (d, J=9 Hz, 1H); 7.06 (d, J=2 Hz, 1H); 7.23 (dd, J=2, 9 Hz, 1H); 7.92 (dd, J=2. 9 Hz, 1H); 8.59 (d, J=2 Hz, 1H).

REFERENCE EXAMPLE 10

Butyl 6-[N-(5-bromo-2-(2-methylpropoxy)benzyl)-N-ethylamino]pyridazine-3-carboxylate Butyl 6-[N-(5-bromo-2-hydroxybenzyl)-N-ethylamino]pyridine-3-carboxylate (reference example 3) (1.12 g, 2.76 mmol) in dimethylformamide (16 ml) was treated with potassium carbonate followed by 1-bromo-2-methylpropane (0.16 ml, 770 mg, 5.6 mmol) and stirred at ambient temperature overnight. TLC showed reaction to be incomplete so further potassium carbonate (1.12 g) and 1-bromo-2-methylpropane were added and the mixture stirred at ambient temperature over two days. The mixture was then evaporated to low bulk and the residue purified directly by MPLC to give the title compound as a colourless gum, (1.26 g 98%).

NMR (250 MHz, DMSO d$_6$) δ 0.90 (m, 9H); 1.15 (t, 3H); 1.42 (m, 2H); 1.70 (m, 2H); 2.03 (m, 1H); 3.73 (q 2H); 3.80 (d, 1H); 4.28 (t, 2H), 4.82 (s, 2H); 6.97 (d, 1H); 7.1 (m, 2H); 7.38 (dd, 1H); 7.81 (d, 1H).

REFERENCE EXAMPLE 11

Butyl 6-[N-(5-chloro-2-hydroxybenzyl)-N-ethylamino]pyridazine-3-carboxylate

The title compound was prepared from butyl 6-(ethylamino)pyridazine-3-carboxylate and 4-chlorophenol using a similar method to that of reference example 3, except 0.4 equivalents of trifluoroacetic acid were added to the reaction mixture.

NMR (250 MHz, DMSO-$d_6$) δ: 0.94 (t, 3H); 1.17 (t, 3H); 1.43 (m, 2H); 1.70 (m, 2H); 3.7 (q, 2H); 4.28 (t, 2H); 4.75 (s, 2H); 6.85 (d, 1H); 6.97 (d, 1H); 7.1 (m, 2H); 7.82 (d, 1H); 10.1 (bs, 1H).

REFERENCE EXAMPLE 12

Butyl 6-[N-(5-chloro-2-(2-methylpropoxy)benzyl)-N-ethyl]pyridazine-3-carboxylate The title compound was prepared by reacting butyl 6-[N-(5-chloro-2-hydroxybenzyl)-N-ethylamino]pyridazine-3-carboxylate (reference example 11) with 1-bromo-2-methylpropane using a similar method to that of reference example 4.

NMR (200 MHz, DMSO-$d_6$) δ: 0.95 (m, 9H); 1.15 (t, 3H); 1.43 (m, 2H); 1.70 (m, 2H); 2.03 (m, 1H); 3.68 (q, 2H); 3.80 (d, 2H); 4.28 (t, 2H); 4.83 (s, 2H); 6.99 (d, 1H); 7.04 (d, 1H); 7.10 (d, 1H); 7.26 (dd, 1H); 7.83 (d, 1H). MS (ES$^+$): 420 (M+H)$^+$.

REFERENCE EXAMPLE 13

N-Ethyl-5-bromo-2-(cyclopropylmethoxy) benzylamine

1-Methyl-2-pyrrolidinone (90 ml) (NMP) was added to anhydrous potassium carbonate (27.6 g, 0.2 mol) under argon. To the stirred mixture was added in portions 5-bromosalicylaldehyde (20.1 ml, 0.1 mol) and the mixture stirred for 10 minutes. Bromomethylcyclopropane (1 4.4 ml, 0.1 5 mol) was dissolved in NMP (10 ml) and added dropwise over 15 minutes below 30° C. The reaction temperature was increased to 35–40° C. for 3 hours. 70° C. for 1 hour and then cooled to 35° C. Ethylamine hydrochloride (13.85 g, 0.17 mol) was dissolved in methanol (60 ml), and added quickly to the mixture which was then heated at 35–40° C. for 3 hours and stirred overnight (allowing it to cool to ambient temperature). The reaction mixture was then cooled in ice. Sodium borohydride (5.3 g, 0.14 mol) was dissolved in NMP (58 ml) and added dropwise [effervescence and exotherm to 15° C] and the mixture heated to 40–45° C. for 2 hours. The reaction mixture was then cooled in ice. 2N Hydrochloric acid (250 mls) was added dropwise keeping the temperature below 30° C. The mixture was transferred to a separating funnel and extracted with ethyl acetate (×2). The combined organic layers were washed with 20% brine/water (×3) and brine (×1). dried over Na$_2$SO$_4$, filtered and evaporated. The residue was dissolved in ethyl acetate (100 ml) and cooled in ice. Hydrogen chloride gas was then bubbled through the stirred solution. The title compound as the hydrochloride salt precipitated and was filtered off, washed with ethyl acetate (×2) and dried under high vacuum (12.6 g, 28.5%).

NMR (200 MHz, DMSO-$d_6$) δ: 0.37 (m, 2H); 0.58 (m, 2H), 1.27 (m, 4H); 2.95 (q, 2H); 3.89 (d, 2H); 4.07 (s, 2H); 7.02 (d, J=8.0 Hz, 1H); 7.53 (dd, J=8.0. 2.9 Hz, 1H); 7.73 (d, J=2.9 Hz, 1H); 9.25 (br s, 2H).

MS (ESP$^+$): 284 (M+H)$^+$.

REFERENCE EXAMPLE 14

6-[N-(5-Bromo-2-(cyclopropylmethoxy)benzyl)-N-ethylamino]-3-cyanopyridazine

6-[N-(5-Bromo-2-cyclopropylmethoxy)benzyl)-N-ethylamino]pyridazine-3-carboxamide (example 11) (2.03 g) was suspended in pyridine (25 ml) and cooled under argon to 4° C. Methanesulphonyl chloride (4.6 ml, 59.5 mmol) was added dropwise (exotherm to −8° C.) followed by pyridine (20 mls). The reaction mixture was allowed to warm and stirred overnight. The pyridine was removed under reduced pressure and the residue partitioned between ethyl acetate and 1N hydrochloric acid. The organic layer was washed with 50% 1N HCl/saturated aqueous ammonium chloride (×I), saturated aqueous sodium bicarbonate (×1) and brine (×1), dried over Na$_2$SO$_4$, filtered and evaporated. The residue was purified by column chromatography, eluting with 2.5% ethyl acetate/dichloromethane and the fractions containing the title product were evaporated to a gum (1.65 g, 85.0%).

NMR (200 MHz, DMSO-$d_6$) δ 0.30 (m,2H); 0.54 (m,2H); 1.15(m,4H); 3.69(q,2H); 3.85(d,2H), 4.80(s,2H); 6.95(d, 1H); 7.20(m,2H); 7.38(dd,1H); 7.80(d,1H).

MS(ESP$^-$): 386.8(M−H)$^-$.

REFERENCE EXAMPLE 15

6-[N-(5-Chloro-2-(2-methylpropoxy)benzyl)-N-ethylamino]-3-cyanopyridazine

6-[N-(5-Chloro-2-(2-methylpropoxy)benzyl)-N-ethylamino]pyridazine-3-carboxylic acid (example 10) (2.0 g) was dissolved in pyridine (30 ml) under argon and cooled to 4° C. Methanesulphonyl chloride (0.75 ml, 9.7 mmol) was added to the mixture which was stirred at 4° C. for 1.5 hours to give a dark purple solution. Ammonia gas was then bubbled through the solution for 2 minutes to give a dark red solution (exotherm to +15° C.) and the solution evaporated under reduced pressure. The residue was dissolved in pyridine (30 ml) and cooled under argon to 4° C. Methanesulphonyl chloride (5.1 ml, 66 mmol) was then added dropwise (exotherm to 10° C.) and the resultant brown suspension stirred at ambient temperature overnight. The brown solution was then evaporated and the residue partitioned between saturated aqueous ammonium chloride and ethyl acetate. The organic layer was washed with 10% 2N HCl/saturated aqueous ammonium chloride (×2), saturated aqueous sodium bicarbonate (×1) and brine (×1), dried over Na$_2$SO$_4$, filtered and evaporated. The title product was isolated by column chromatography using 20% ethyl acetate/isohexane as eluant (1.18 g, 62.2%). [OPPI 14: 396–9 (1982)].

NMR(200 MHz, DMSO-$d_6$) δ: 0.97(d,6H); 1.12(t,3H); 2.00(m,1H); 3.67(q,2H); 3.79(d,2H); 4.85(s,2H); 7.05(m, 2H); 7.19(d,1H); 7.29(dd,1H); 7.84(d,1H).

MS(ES$^+$): 345 (M+H)$^+$.

REFERENCE EXAMPLE 16 n-Butyl 6-[N-(5-bromo-2-(2-hydroxy-3,3,3-trifluoropropoxy)benzyl)-N-ethylamino]pyridazine-3-carboxylate The title compound was prepared by reacting 3-bromo-1,1,1-trifluoropropan-2-ol and butyl 6-[N-(5-bromo-2-hydroxybenzyl)-N-ethylamino]pyridazine-3-carboxylate using a similar method to that of reference example 4.

NMR: (250 MHz, DMSO-$d_6$) δ: 0.95(t,3H); 1.15(t,3H); 1.42(m,2H); 1.68(m,2H); 3.7(q,2H); 4.20(m,4H); 4.42(m, 1H); 4.83(s,2H); 6.65(d,1H); 7.1(m,3H); 7.42(dd,1H); 7.63 (d,1 H).

REFERENCE EXAMPLE 17

6-[N-(2-(Cyclopropylmethoxy)-5-methanesulphonylbenzyl)-N-ethylamino]-3-cyanopyridazine 4-Methyl mercaptophenol (8.96 g, 64 mmol) suspended in toluene (80 ml) was added to magnesium methoxide solution in methanol (5.5 ml, 8% soln, 41.4 mmol) and the reaction stirred at reflux for 1 hour. After this time the yellow solution was treated with toluene (80 ml) and methanol distilled from the reaction until reaction temperature reached approximately 95° C. Some solid precipitated. Paraformaldehyde (5.84 g, 194 mmol) in toluene (60 ml) was added to the mixture. which was stirred at reflux for 3.5 hours under argon (the temperature must be at least 95° C.). The reaction mixture containing a little solid was then cooled and treated with 2N sulphuric acid (80 ml), toluene (80 ml), stirred for 15 minutes and separated. The organic layer was washed with water (×3), dried and evaporated to leave an orange oil (9.6 g). This oil was purified by MPLC using 5% ether/isohexane to give 2-hydroxy-5-methylthiobenzaldehyde (3.3 g).

NMR (200 MHz, DMSO-$d_6$) δ: 2.45(s,3H); 6.98(d,J=9 Hz, 1H); 7.48(dd, J=2.3, 9.0 Hz, 1H); 7.55(d,J=2.3 Hz, 1H); 10.25(s,1H); 10.67(s,1H).

MS (CI+): 168($M^+$).

2-Hydroxy-5-methylthiobenzaldehyde was alkylated with bromomethylcyclopropane using a similar method to that of reference example 4 to give 2-cyclopropylmethoxy-5-methylthiobenzaldehyde.

NMR(200 MHz, DMSO-$d_6$) δ: 0.36(m,2H); 0.6(m,2H); 1.26(m,1H); 2.46(s,3H); 4.0(d,J=8.25 Hz,2H); 7.2(d,J=9.2 Hz, 1H); 7.52–7.62(m,2H); 10.38(s,1H);

MS ($CI^+$): $(M+H)^+$ 223.3.

N-Ethyl 2-cyclopropylmethoxy-5-methylthiobenzylamine was prepared by reductive amination of 2-cyclopropylmethoxy-5-methylthiobenzylamine using a similar method to that of reference example 19(1).

NMR(200 MHz, DMSO-$d_6$) δ: 0.32(m,2H); 0.55(m,2H); 1.03(t,J=7.3 Hz, 3H); 1.30–1.13(m,1H); 2.4(s,3H), 2.53(q, J=7.3 Hz, 2H); 3.65(s,2H), 3.82(d,J=6.25 Hz, 2H); 6.88(d, J=8.3 Hz, 1H), 7.10(dd, J=2.5, 8.3 Hz, 1H), 7.25(d, J=2.5 Hz, 1H).

MS ($ESP^+$); 252.4$(M+H)^+$.

N-Ethyl 2-cyclopropylmethoxy-5-methylthiobenzylamine was reacted with 3-chloro-6-cyanopyridazine (prepared in reference example 18) using a similar method to that of example 11 to give 6-[N-(2-cyclopropylmethoxy)-5-methylthiobenzyl)-N-ethylamino]-3-cyanopyridazine.

NMR(200 MHz, DMSO-$d_6$) δ: 0.28(m,2H); 0.52(m,2H); 1.20–1.08(m,4H); 2.35(s,3H); 3.70(q,2H); 3.84(d, J=8.3 Hz,2H); 4.8(s,2H); 6.95(d, J=8.3 Hz,1H); 7.03(d, J=2.1 Hz,1H); 7.19(dd, J=10.4, 2.1 Hz, 2H); 7.8(d, J=10.4 Hz, 1H).

MS (ESP+): 355$(M+H)^+$.

6-[N-(2-Cyclopropylmethoxy-5-methylthiobenzyl)-N-ethylamino]-3-cyanopyridazine (201 mg, 0.57mmol) in dichloromethane (5 ml) was cooled on ice to approximately −10° C. and treated with 50% m-chloroperbenzoic acid (196 mg, 0.57 mmol). The reaction mixture was stirred at −10 to 0° C. for 1 hour, then diluted with dichloromethane and extracted with saturated aqueous sodium bicarbonate solution (×2). The organic extracts were dried and evaporated to give a pale brown foam (1 80 mg). The foam (1 80 mg, 0.49 mmol) in dichloromethane (5 ml) was cooled to −10° C., treated with m-chloroperbenzoic acid (1 70 mg, 0.49 mmol) and stirred for 1.25 hours as the temperature rose to 0° C. More dichloromethane was added and the mixture extracted with saturated aqueous sodium bicarbonate solution (×2). dried and evaporated to give a foam which was purified by MPLC using 2:1 ethyl acetate/hexane as eluant to yield the title product (100 mg, 53%).

NMR (200 MHz, DMSO-$d_6$) δ: 0.32(m,2H), 0.54(m,2H); 1.27–1.08(m,4H); 3.08(s,3H); 3.7(q,2H); 3.98(d, J=8.3 Hz,2H); 4.88(s,2H); 7.22(d, J=10.4 Hz,1H); 7.26(d, J=10.4, Hz, 1H); 7.61(d, J=2.1 Hz, 1H); 7.77–7,78(m, J=10.21 Hz, 2H);

MS($ESP^+$) $(M+H)^+$ 387.2.

REFERENCE EXAMPLE 18

6-[N-(5-Bromo-2-propoxybenzyl)-N-ethylamino]-3-cyanopyridazine (1) A mixture of 6-chloropyridazine-3-carboxamide (described in reference example 3) (15 g, 95.5 mmol) and pyridine (22.6 g, 23.1 ml, 286.6 mmol) were was suspended in dichloromethane and cooled to −30° C. under argon. TFAA was added dropwise to the stirred mixture keeping the internal temperature below −20° C. The reaction was stirred for 19.5 hours allowing to warm to ambient temperature. The mixture was poured into water(500 ml) and washed with water (4×500 ml) until the aqueous phase was pale yellow. The organic phase was dried over $MgSO_4$, filtered through a pad of silica (50 mm diameter, 30 mm deep), and concentrated in vacuo. The resulting solid was purified by MPLC (40% dichloromethane/20%ethyl acetate/hexane) to give 3-chloro-6-cyanopyridazine as a colourless solid (5.25 g, 59%).

MS (EI+): 139 ($M^+$)

NMR (250 MHz, $CDCl_3$) δ: 7.71 (d, J=8 Hz, 1H); 7.83 (d, J=8 Hz, 1H).

(2) A solution of 5-bromosalicyladehyde (20 g, 100 mmol) in NMP (100 ml) was treated with $K_2CO_3$ (41.4 g, 300 mmol) at 40° C. for 30 minutes. n-Propyl iodide (25.5 g, 150 mmol) was added and the reaction mixture stirred at 40° C. for 19 hours. A solution of ethylamine hydrochloride (11.41 g, 140 mmol) in ethanol (50 ml) was added and the mixture stirred at 40° C. for a further 3hours, after which a solution of sodium borohydride (5.292 g, 140 mmol) in NMP (20 ml) was added dropwise over 1 hour (CAUTION: much foaming). The reaction was stirred at 40° C. for 19 hours cooled to ambient temperature and 5M hydrochloric acid (500 ml). The solution was then treated with 5M sodium hydroxide solution to pH 14 and extracted with ethyl acetate (3×300 ml). The combined organic phases were washed with water (4×500 ml) dried over potassium carbonate and dry HCl gas was passed over the solution. The slurry was concentrated in vacuo to give a yellow solid which was recrystallised from acetonitrile/toluene to give N-ethyl 2-propoxy-5-bromobenzylamine hydrochloride as a white solid. (15.47 g. 50%).

MS (ESP): 375 ($MH^-$).

NMR (250 MHz, $CDCl_3$) δ: 1.02 (t, J=7 Hz, 3H); 1.25 (t, J=6 Hz, 3H); 1.80 (m, 2H); 3.77 (q, J=6 Hz, 2H); 3.92 (t, J=7 Hz, 2H); 4.80 (brs, 2H); 6.67 (d, J=8.5 Hz, 1H); 6.75 (d, J=Hz, 1H); 7.12 (d, J=2 Hz, 1H); 7.34 (dd, J=8.2 Hz, 1H); 7.38 (d, J=8.5 Hz, 1H).

(3) N-ethyl 2-propoxy-5-bromobenzylamine hydrochloride 2 (5.17 g, 16.8 mmol) and 3-chloro-6-cyanopyridazine (2.65 g, 16.8 mmol) were dissolved in NMP (25 ml) and sodium hydrogen carbonate added (3.54 g, 42.1 mmol). The mixture was heated at 110° C. under argon for 7.5 hours and then allowed to cool to ambient temperature. The mixture was poured into ethyl acetate (200 ml) washed with water (5×200 ml) and brine (200 ml), the organic phase dried over $MgSO_4$ and concentrated in vacuo. The residue was purified by MPLC (20%ethyl acetate/hexane) and then crystallised from ether/hexane to give the title product (4.80 g, 76%).

MS (ESP): 272 (MH⁺), 227 (M–EtNH₂)⁺.

NMR (250 MHz, DMSO-d₆) δ: 0.99 (t, J=6 Hz, 3H); 1.26 (t, J=7 Hz, 3H); 1.78 (m, 2H); 2.92 (q, J=7 Hz, 2H); 3.95 (t, J=6 Hz, 2H); 4.02 (s, 2H); 7.02 (d, J=8 Hz, 1H); 7.52 (dd, J=8, 2 Hz, 1H); 7.75 (d, J=2 Hz, 1H); 9.32 (brs, 2H).

REFERENCE EXAMPLE 19

6-[N-(5-Bromo-2-hydroxybenzyl)-N-ethylamino]-3-cyanopyridazine (1) A solution of 5-bromo salicylaldehyde (20.1 g 0.1 mmol) in THF (150 ml) was treated with a solution of ethylamine in methanol (2M, 70 ml, 0.14 mmol). The reaction was stirred at ambient temperature for 1.5 hours. After cooling in an ice bath, sodium borohydride (5.3 g, 0.14 mmol) was added portionwise. The reaction was allowed to stand at ambient temperature overnight. Water was added and the solvent removed at reduced pressure. The residue was dissolved in ethyl acetate and washed with water and the organic layer dried over MgSO4 and acidified with gaseous HCl. N-Ethyl-5-bromo-2-hydroxybenzylamine hydrochloride was collected by filtration as a white solid. (17.53 g, 66%).

NMR (250 MHz DMSO-d₆) δ: 1.23(t,3H) 2.94(q,2H); 4.60(t,2H); 6.96(d, H); 7.37(dd, H); 7.63(d,1H); 9.02(bs. H); 1 0.59(s,1H).

MS(ESP⁺): 230/232 (M+H)⁺.

(2) The title compound was prepared by reacting N-ethyl-5-bromo-2-hydroxybenzylamine hydrochloride and 3-chloro-6-cyanopyridazine using a similar method to that of reference example 18 except eluting with 2% diethyl ether/dichloromethane in the chromatography (yield 50%).

NMR (250 MHz, DMSO-d₆) δ 1.15(t,3H); 8.37(q,2H); 4.75(s,2H); 6.81(d,1H); 7.07(d,1H); 7.15(d,1H); 7.25(dd, H); 7.82(d,1H); 10.12(bs,1H).

REFERENCE EXAMPLE 20

N-Ethyl-5-chloro-2-(cyclopropylmethoxy)benzylamine

The title compound was prepared by reacting 5-chloro-2-hydroxybenzaldehyde with bromomethylcyclopropane using a similar method to reference example 4.

MS (CI⁺): 240/242 (M+H)⁺.

NMR (200 MHz, CDCl₃) δ0.34(m,2H); 0.63(m,2H); 1.13 (t, J=7 Hz, 23H); 1.26(m,1H); 2.65(q, J=7 Hz, 2H); 3.78(d, 2H); 3.80(d,2H); 6.72(d, J=8 Hz, 1H); 7.13(dd, J=2, 8 Hz, 1H); 7.21(d, J=2 Hz, 1H).

REFERENCE EXAMPLE 21

6-[N-(5-Chloro-2-(cyclopropylmethoxy)benzyl)-N-ethylamino]-3-cyanopyridazine

To a stirred mixture of 6-[N-(5-chloro-2-(cyclopropylmethoxy)benzyl)-N-ethylamine]pyridazine-3-carboxamide (3.5 g, 9.7 mmol in pyridine (120 ml) at 20° C., was added dropwise during 20 minutes, methane sulphonyl chloride (10.0 ml, 124 mmol). The mixture was stirred at 20° C. for 60 hours and poured onto ice (300 gm) and 10N hydrochloric acid (100 ml), stirring vigorously, then extracted with ether (500 ml). The organic layer was washed with 1N hydrochloric acid (500 ml), dried over anhydrous magnesium sulphate and evaporated to give the title product as a light brown gum, (3.3 g, 99%).

MS (ESP⁺): 343/345 (M+H)⁺.

NMR (200 MHz, CDCl₃) δ 0.32(m,2H); 0.60(m,2H), 1.20 (m,1H); 1.25(t, J=7 Hz, 3H); 3.82 (d,2H); 3.85(q, J=7 Hz, 2H); 4.85(s, 2H); 6.78(d, J=8 Hz, 1H); 7.06(d, J=8 Hz, 1H); 7.09(d, J=2 Hz, 1H); 7.22(dd, J=2, 8 Hz, 1H); 7.52(d, J=8 Hz, 1H).

REFERENCE EXAMPLE 22

N-Ethyl 5-chloro-2-(cyclopentoxy)benzylamine

To 5-chlorosalicylaldehyde (20.3 g, 130 mmol) and bromocyclopentane (22.0 g, 148 mmol) in dimethylformamide (100 ml) was added anhydrous potassium carbonate (23.4 g, 169 mmol) and the solution stirred at 50° C. for 16 hours. The inorganic solid was extracted and the solvent removed in vacuo. The product was extracted into dichloromethane from water (200 ml) and the organic layer subsequently dried over anhydrous magnesium sulfate, filtered and the solvent removed under reduced pressure. The redissolved product was purified by flushing through a silica plug (dichloromethane) and washing with 2 normal sodium hydroxide solution (100 ml×3) to yield 5-chloro-2-cyclopentoxybenzaldehyde. (19.22 g, 66%).

M.S. (CI⁺): 225/227 (MH+).

NMR. (200 MHz, DMSO-d₆) d: 1.80 (m, 8H); 4.98 (m,1H); 7.24 (d, J=8 Hz, 1H); 7.58 (d, J=2 Hz, 1H); 7.62 (dd, J=2.8 Hz, 1H); 10.28 (s, 1H).

5-Chloro-2-cyclopentoxybenzaldehyde (9.35 g, 41.6 mmol) and ethylamine hydrochloride (18.6 g, 229 mmol) in methanol (100 ml) for 30 minutes at ambient temperatures, following which sodium cyanoborohydride (5.6 g, 88 mmol) was added and the reaction left to reflux at 70° C. for 70 hours with periodic acidification to pH 6 using glacial acetic acid. Normal hydrochloric acid (100 ml) was added in a dropwise fashion and the resultant mixture basified with 2 normal sodium hydroxide solution until a pH of 11 existed, whereupon the product was extracted into dichloromethane (250 ml×2) and ethyl acetate (250 ml×2). The organic layers were combined, dried over anhydrous magnesium sulfate, filtered and the solvent removed to yield the title compound (8.5 g, 80%).

REFERENCE EXAMPLE 23

6-(N-[5-Chloro-2-(cyclopentoxy)benzyl]-N-ethylamino)-3-cyanopyridazine

The title compound was prepared by reacting reference example 22 and 3-chloro-6-cyanopyridazine (reference example 18(1)) using a similar method to that of reference example 18(3).

REFERENCE EXAMPLE 24

6-[N-(5-Bromo-2-(cyclobutyloxy)benzyl)-N-ethylamino]-3-cyanopyridazine

The title compound was prepared by alkylation of the appropriate nitrile (reference example 18) with bromocyclobutane using a similar method to that of reference example 4, except that the reaction was stirred at ambient temperature for 10 days.

MS (ESP)⁺: 387 (M+H)⁺.

NMR (250 MHz, DMSO-d₆)δ: 1.14(t, 3H); 1.73 (m, 2H); 1.98(m 2H); 2.40(m, 2H); 3.68 (q, 2H); 4.72 (quintet, 1H); 4.81 (s, 2H); 6.82(d, 1H); 7.2(m, 2H); 7.37 (dd, 1H); 7.83(d, 1H).

REFERENCE EXAMPLE 25

6-[N-(5-Bromo-2-(3,3,3-trifluoro-2-hydroxypropoxy)benzyl)-N-ethylamino]-3-cyanopyridazine The title compound was prepared by reacting 6-[N-(5-bromo-2-hydroxybenzyl)-N-ethylamino]-3- cyanopyridazine with 1,1,1-trifluoro-3-bromo-propan-2-ol using a method similar to that of reference example 4.

M.S. (ESP)+: 445 (M+H)+.

NMR: (250 MHz, DMSO-d$_6$) δ: 1.15 (t 3H); 3.68(q, 2H); 4.16 (m, 1H); 4.25 (m, 1H); 4.4(m, 1H); 4.85(s, 2H); 6.65(d, 1H); 7.14(m, 3H); 7.43(dd, 1H); 7.83 (d, 1H).

REFERENCE EXAMPLE 26

2-[N-(5-Bromo-2-cyclopropylmethoxybenzyl)-N-ethylamino]-5-cyanopyridine

The title compound was prepared by reacting N-ethyl-5-bromo-2-cyclopropylmethoxybenzylamine (reference example 13) and 2-chloro-5-cyanopyridine using a similar method to that of reference example 18.

MS: 386 (M+H)+.

NMR (MHz, DMSO-d$_6$) δ: 0.33 (m, 2H); 0.55 (m, 2H); 1.15 (m, 4H); 3.60 (q, 2H); 3.88 (d, 2H); 4.75 (s, 2H); 6.70(d 1H); 6.95 (d, 1H); 7.05 (d, 1H); 7.35 (dd, 1H); 7.75 (dd, 1H); 8.45 (d, 1H).

REFERENCE EXAMPLE 27

6-[N-(5-Chloro-2-cyclobutylmethoxybenzyl)-N-ethylamino]-3-cyanopyridazine

Cyclobutanemethanol(5 g, 58 mmol) was dissolved in dichloromethane (150 ml) and cooled in an ice water bath. Triethylamine (10.5 ml,-75.5 mmol) was added followed by the dropwise addition of a solution of tosyl chloride (13.3 g, 69.8 mmol) in dichloromethane (50 ml). The cooling bath was removed and the mixture allowed to warm to room temperature over 16 hours. The mixture was washed with water (2×100 ml) dried (MgSO$_4$) and concentrated in vacuo to give cyclobutanemethanol tosylate as a yellow oil which was used without further purification.

MS: 241 (M+H)+.

5-Chlorosalicylaldehyde (7.7 g, 49.4 mmol) was dissolved in DMF (20 ml) with potassium carbonte (7.5 g, 54.1 mmol) and the cyclobutanemethanol tosylate (1 3 g, 54.1 mmol). The mixture was stirred at 50° C. under argon for 16 hours. Poured into water (500 ml). extracted with ethyl acetate (4×100 ml)and the combined organic fractions washed with 1M sodium hydroxide solution (100 ml), water (100 ml), saturated brine (100 ml) dried (MgSO$_4$) and concentrated in vacuo to give 5-chloro-2-(cyclobutylmethoxy)benzaldehyde as a brown oil (13 g) which was used without further purification.

MS: 225 (M+H)+.

5-chloro-2-(cyclobutylmethoxy)benzaldehyde (13 g) was dissolved in DMF (100 ml) and potassium carbonate (16 g, 116 mmol) added followed by ethylamine hydrochloride (9.5 g, 117 mmol). The mixture was heated at 40° C. for 1 hour then cooled in an ice water bath and a solution of sodium borohydride (4.3 g, 116 mmol) in minimal DMF added dropwise. When addition was complete the cooling bath was removed and the reaction mixture heated to 40° C. for 16 hours. The reaction was cooled to room temperature and 5M hydrochloric acid added cautiously until the mixture was at pH 2. Solid sodium hydroxide was then added to adjust the pH to 14 and the mixture was extracted with ethyl acetate (3×300 ml) the combined organic fractions washed with water (100 ml), saturated brine (100 ml) dried (MgSO$_4$) and concentrated in vacuo to give an oil (15 g). This oil purified by MPLC (5% methanol/dichloromethane) to give N-ethyl 5-chloro-2-(cyclobutylmethoxy)benzylamine as a gum which crystallised on standing (2.1 g, 17%).

MS: 254 (M+H)+.

NMR (MHz, DMSO-d$_6$) δ: 1.05(t, 3H); 1.95 (m, 6H); 2.50(m, 1H); 2.75 (q, 2H); 3.65 (s, 2H); 3.92 (d, 2H); 6.95(d, 1H); 7.20 (dd, 1H); 7.28 (d, 1H).

N-Ethyl 5-chloro-2-(cyclobutylmethoxy)benzylamine (2.1 g, 8.3 mmol) was coupled to the 3-chloro-5-cyanopyridazine (1.3 g, 8.25 mmol) with sodium hydrogen carbonate (0.71 g. 8.45 mmol) in NMP (10 ml) in a similar method to that of reference example 18. The title compound was purified by MPLC (dichloromethane, 1% MeOH/dichloromethane) (2.3 g, 78%) to give a solid.

MS: 357 (M+H)+.

NMR (MHz, DMSO-d$_6$) δ: 1.1 (t, 3H); 1.95 (m, 6H); 2.60(m, 1H); 3.65 (q, 2H); 3.95 (d, 2H); 4.8 (s, 2H); 6.95(d, 1H); 7.00 (d, 1H); 7.18 (d, 1H); 7.26(dd, 11H); 7.82 (d, 1H).

REFERENCE EXAMPLE 28

N-Ethyl-5-bromo-2-(cyclopropylmethoxy)benzylamine

To 5-bromosalicylaldehyde (15.0 g, 74 mmol) in dimethylformamide was added anhydrous potassium carbonate (36.8 g, 266 mmol) and bromomethylcyclopropane (9 ml, 93 mmol) and the solution stirred at 50° C. for 60 hours. Propylamine (26.5 g, 450 mmol) was then added and the solution left to stir at ambient temperatures for 2 hours, afterwhich diethyl ether (50 ml) and sodium borohydride (2.6 g, 68 mmol) were added and the solution left for another hour. 6 Normal hydrochloric acid (150 ml) was then added dropwise and the solution left to stir for 16 hours. Impurities were extracted with diethyl ether (200 ml×2), the solution basified with caustic liquor and the product then extracted into diethyl ether (250 ml). The organic layer was then dried over anhydrous magnesium sulphate, filtered and the solvent removed in vacuo to give the title compound (4.8 g, 22%).

MS (EI+): 298/300 (MH+).

NMR (200 MHz, DMSO-d$_6$) δ: 0.34 (m,2H); 0.56 (m,2H); 0.88 (t, 3H); 1.22 (m, 1H); 1.44 (m, 2H), 2.47 (t, 2H); 3.66 (s, 2H), 3.82 (d, 2H); 6.86 (d, J=8 Hz, 1H); 7.31 (dd, J=2 Hz, 8 Hz, 1 H), 7.46 (d, J2 Hz, 1 H).

I claim:

1. A compound of formula (I):

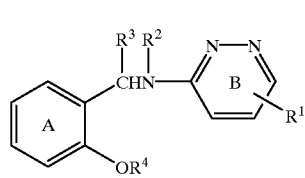

wherein:
ring A is unsubstituted or substituted, provided that the —CH(R³)N(R²)B—R¹ and —OR⁴ groups are positioned in a 1,2 relationship to one another on ring atoms, and the ring atom positioned ortho to the OR⁴ group (and therefore in the 3-position relative to the —CH(R³)N(R²)— linking group) is not substituted, where:
ring A substituents are selected from halo, trifluoromethyl, nitro, hydroxy, amino, (C$_1$–C$_4$)alkylamino, di(C$_1$–C$_4$) alkylamino, cyano, (C$_1$–C$_6$)alkoxy, (C$_1$–C$_6$)alkylS(O)$_p$-where p is 0, 1 or 2; (C$_1$–C$_6$)alkyl optionally substituted with hydroxy, amino, halo, nitro or cyano; CF$_3$S(O)$_p$-where p is 0, 1 or 2; carbamoyl, (C$_1$–C$_4$)

alkylcarbamoyl, di($C_1$–$C_4$)alkylcarbamoyl, ($C_2$–$C_6$) alkenyl, ($C_2$–$C_6$)alkynyl, ($C_1$–$C_4$) alkoxycarbonylamino, ($C_1$–$C_4$)alkanoylamino, ($C_1$–$C_4$)alkanoyl(N-($C_1$–$C_4$)alkyl)amino, ($C_1$–$C_4$) alkanesulphonamido, benzenesulphonamido, aminosulphonyl, ($C_1$–$C_4$)alkylaminosulphonyl, ($C_1$–$C_4$)alkanoylaminosulphonyl, di($C_1$–$C_4$) alkylaminosulphonyl, ($C_1$–$C_4$)alkoxycarbonyl, ($C_1$–$C_4$)alkanoyloxy, ($C_1$–$C_6$)alkanoyl, formyl($C_1$–$C_4$) alkyl, trifluoro($C_1$–$C_3$)alkylsulphonyl, hydroxyimino ($C_1$–$C_6$)alkyl, ($C_1$–$C_4$)alkoxyimino($C_1$–$C_6$)alkyl and ($C_1$–$C_6$)alkylcarbamoylamino;

ring B is unsubstituted or substituted, where:

ring B substituents are selected from halo, trifluoromethyl, nitro, hydroxy, ($C_1$–$C_6$)alkoxy, ($C_1$–$C_6$)alkyl, amino, ($C_1$–$C_4$)alkylamino, di($C_1$–$C_4$) alkylamino, cyano, ($C_1$–$C_6$)alkyl S(O)$_p$— where p is 0, 1 or 2; carbamoyl, ($C_1$–$C_4$)alkylcarbamoyl and di($C_1$–$C_4$)alkylcarbamoyl $R^1$ is positioned on ring B in a meta or para relationship with the —CH($R^3$)N($R^2$)— linking group; and $R^1$ is selected from carboxy, carboxy($C_1$–$C_3$)alkyl, tetrazolyl, tetrazolyl($C_1$–$C_3$)alkyl, tetronic acid, hydroxamic acid and sulphonic acid; or $R^1$ is of the formula —CONR$^a$R$^{a1}$, wherein R$^a$ is hydrogen or ($C_1$–$C_6$)alkyl, and R$^{a1}$ is hydrogen, ($C_1$–$C_6$) alkyl optionally substituted by halo, amino, ($C_1$–$C_4$) alkylamino, di($C_1$–$C_4$)alkylamino, hydroxy, nitro, cyano, trifluoromethyl, ($C_1$–$C_4$)alkoxy or ($C_1$–$C_4$) alkoxycarbonyl; ($C_2$–$C_6$)alkenyl provided the double bond is not in the 1-position; ($C_2$–$C_6$)alkynyl provided the triple bond is not in the 1-position; carboxyphenyl, 5- or 6-membered heterocyclyl($C_1$–$C_3$)alkyl, 5- or 6-membered heteroaryl($C_1$–$C_3$)alkyl, 5- or 6-membered heterocyclyl, or 5- or 6-membered heteroaryl, or R$^a$ and R$^{a1}$ together with the amide nitrogen to which they are attached form an amino acid residue or ester thereof; wherein any heterocyclyl or heteroaryl group in R$^{a1}$ is optionally-substituted by halo, hydroxy, nitro, cyano, trifluoromethyl, ($C_1$–$C_4$) alkoxy or ($C_1$–$C_4$)alkoxycarbonyl,; or $R^1$ is of the formula —CONHSO$_2$R$^b$, wherein R$^b$ is ($C_1$–$C_6$)alkyl optionally substituted by halo, hydroxy, nitro, cyano, trifluoromethyl, ($C_1$–$C_4$)alkoxy, amino, ($C_1$–$C_4$)alkylamino, di($C_1$–$C_4$)alkylamino or ($C_1$–$C_4$) alkoxycarbonyl; ($C_2$–$C_6$)alkenyl provided the double bond is not in the 1-position; ($C_2$–$C_6$)alkynyl provided the triple bond is not in the 1-position; 5- or 6-membered heterocyclyl($C_1$–$C_3$)alkyl, 5- or 6-membered heteroaryl($C_1$–$C_3$)alkyl, phenyl($C_1$–$C_3$) alkyl, 5- or 6-membered heterocyclyl, 5- or 6-membered heteroaryl or phenyl; wherein any phenyl, heterocyclyl or heteroaryl group in R$^b$ is optionally-substituted by halo, trifluoromethyl, nitro, hydroxy, amino, cyano, ($C_1$–$C_6$)alkoxy, ($C_1$–$C_6$)alkyl-S(O)$_p$— where p is 0, 1 or 2; ($C_1$–$C_6$)alkyl, carbamoyl, ($C_1$–$C_4$) alkylcarbamoyl, di($C_1$–$C_4$)alkylcarbamoyl, ($C_2$–$C_6$) alkenyl, ($C_2$–$C_6$)alkynyl, ($C_1$–$C_4$) alkoxycarbonylamino, ($C_1$–$C_4$)alkanoylamino, ($C_1$–$C_4$)alkanoyl(N-($C_1$–$C_4$)alkyl)amino, ($C_1$–$C_4$) alkanesulphonamido, benzenesulphonamido, aminosulphonyl, ($C_1$–$C_4$)alkylaminosulphonyl, di($C_1$–$C_4$)alkylaminosulphonyl, ($C_1$–$C_4$) alkoxycarbonyl, ($C_1$–$C_4$)alkanoyloxy, ($C_1$–$C_6$) alkanoyl, formyl($C_1$–$C_4$)alkyl, hydroxyimino($C_1$–$C_6$) alkyl, ($C_1$–$C_4$)alkoxyimino($C_1$–$C_6$)alkyl or ($C_1$–$C_6$) alkylcarbamoylamino; or $R^1$ is of the formula —SO$_2$N(R$^c$)$_2$, wherein R$^c$ at each occurrence is selected from hydrogen and ($C_1$–$C_4$) alkyl; or $R^1$ is of formula (IA), (IB) or (IC):

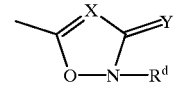
(IA)

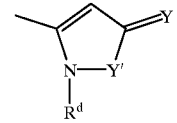
(IB)

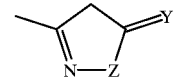
(IC)

wherein:
in compounds of Formula (IA), X is CH or nitrogen,
in compounds of Formula (IA), (IB) or (IC), Y is oxygen or sulphur,
in compounds of Formula (IC), Z is CH$_2$, NR$^d$ or oxygen,
in compounds of Formula (IB), Y' is oxygen or NR$^d$, and
in compounds of Formula (IA), (IB) or (IC), R$^d$ is hydrogen or ($C_1$–$C_4$)alkyl, provided that compounds of formulae (IA), (IB) and (IC) each have no more than one ring oxygen and at least two ring heteroatoms;

$R^2$ is selected from hydrogen, ($C_1$–$C_6$)alkyl optionally substituted by hydroxy, cyano or trifluoromethyl; ($C_2$–$C_6$)alkenyl provided the double bond is not in the 1-position; ($C_2$–$C_6$)alkynyl provided the triple bond is not in the 1-position; phenyl($C_1$–$C_3$)alkyl and pyridyl ($C_1$–$C_3$)alkyl;

$R^3$ is selected from hydrogen, methyl or ethyl;

$R^4$ is selected from optionally substituted ($C_1$–$C_6$)alkyl, optionally substituted ($C_3$–$C_7$)cycloalkyl($C_1$–$C_3$)alkyl and optionally substituted ($C_3$–$C_7$)cycloalkyl;

an N-oxide of —NR$^2$, where chemically possible;

an S-oxide of sulphur containing rings, where chemically possible;

or a pharmaceutically-acceptable salt thereof.

2. A compound according to claim 1, wherein R$^3$ is hydrogen.

3. A compound according to claim 1, wherein R$^2$ is selected from hydrogen, methyl, ethyl and propyl.

4. A compound according to claim 1, wherein:
$R^1$ is selected from carboxy, carbamoyl and tetrazolyl, or
$R^1$ is of the formula —CONR$^a$R$^{a1}$ wherein R$^a$ is hydrogen or ($C_1$–$C_6$)alkyl and R$^{a1}$ is selected from ($C_1$–$C_6$) alkyl optionally substituted by hydroxy, ($C_2$–$C_6$) alkenyl, 1-morpholinyl, 1-piperidinyl, 1-pyrrolidinyl and pyridyl($C_1$–$C_3$)alkyl, or
$R^1$ is of the formula —CONHSO$_2$R$^b$ wherein R$^b$ is selected from optionally substituted ($C_1$–$C_6$)alkyl, phenyl and 5- or 6-membered heteroaryl.

5. A compound according to claim 1, wherein:
$R^1$ is of the formula —CONHR$^{a1}$ wherein R$^{a1}$ is selected from pyridylmethyl and ($C_1$–$C_4$)alkyl optionally substituted by hydroxy, or
$R^1$ is of the formula —CONHSO$_2$R$^b$ wherein R$^b$ is selected from ($C_1$–$C_4$)alkyl, 3,5-dimethylisoxazol-4-yl and 5-acetamido-1,3,4-thiadiazol-2-yl.

6. A compound according to claim 1, wherein ring A is substituted with halo, nitro, trifluoromethyl, cyano, amino, $(C_1-C_6)$alkoxy, carbamoyl, $(C_1-C_4)$alkylcarbamoyl, di$(C_1-C_4)$alkylcarbamoyl, $(C_1-C_4)$alkanoylamino, $(C_1-C_6)$ alkylS(O)$_p$, $(C_1-C_4)$alkanesulphonamido, benzenesulphonamido, $(C_1-C_6)$alkanoyl, $(C_1-C_4)$ alkoxyimino$(C_1-C_4)$alkyl or hydroxyimino$(C_1-C_4)$alkyl.

7. A compound according to claim 1, wherein ring B is substituted with halo, trifluoromethyl, $(C_1-C_4)$alkyl, amino, $(C_1-C_4)$alkylamino, di$(C_1-C_4)$alkylamino, nitro, hydroxy, $(C_1-C_6)$alkoxy or cyano.

8. A compound according to claim 1, wherein $R^4$ is selected from optionally substituted $(C_1-C_4)$alkyl, $(C_3-C_6)$ cycloalkyl and $(C_3-C_6)$cycloalkylmethyl.

9. A pharmaceutical composition which comprises a compound according to claim 1, and a pharmaceutically-acceptable carrier.

10. A process for preparing a compound according to claim 1, which comprises deprotecting a compound of the formula (III):

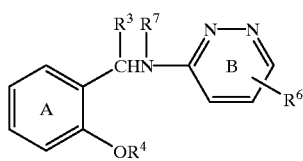

(III)

wherein:
$R^6$ is $R^1$ as defined in claim 1, or protected $R^1$,
$R^7$ is $R^2$ as defined in claim 1, or protected $R^2$ and,
$R^3$, $R^4$, A and B are as defined in claim 1, and any optional substituents are optionally protected and at least one protecting group is present;
and thereafter if necessary:
i) converting one optional substituent into another optional substituent, and
ii) forming a pharmaceutically-acceptable salt.

11. A process for preparing a compound according to claim 1, or a compound of the formula (III) as defined in claim 8, which comprises:
a) reacting a compound of the formula (V) with a compound of the formula (VI):

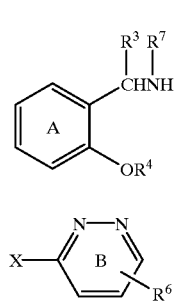

wherein:
$R^6$ is $R^1$ as defined in claim 1, or protected $R^1$;
X is a leaving group;
$R^7$ is hydrogen or $(C_1-C_6)$alkyl, and
$R^3$ and $R^4$ are as defined in claim 1, and any optional substituents are optionally protected and at least one protecting group is present;

and thereafter if necessary;
i) removing said protecting groups;
ii) forming a pharmaceutically-acceptable salt;
iii) converting an optional substituent into another optional substituent.

12. A compound of formula (III) as defined in claim 8.
13. A compound according to claim 1, which is:
6-[N-(5-bromo-2-(cyclopropylmethoxy)benzyl)-N-ethylamino]pyridazine-3-carboxylic acid;
6-[N-(5-bromo-2-propoxybenzyl)-N-ethylamino] pyridazine-3-carboxylic acid;
6-[N-(5-bromo-2-n-butoxybenzyl)-N-ethylamino] pyridazine-3-carboxylic acid;
N-(3,5-dimethylisoxazol-4-ylsulphonyl)-6-[N-(5-bromo-2-(cyclopropylmethoxy)benzyl)-N-ethylamino]pyridazine-3-carboxamide;
N-(3,5-dimethylisoxazol-4-ylsulphonyl)-6-[N-(5-chloro-2-(2-methylpropoxy)benzyl)-N-ethylamino]pyridazine-3-carboxamide;
N-(2-acetamidothiadiazol-5-ylsulphonyl)-6-[N-(5-chloro-2-(2-methylpropoxy)benzyl)-N-ethylamino]pyridazine-3-carboxamide;
N-propanesulfonyl-6-[N-(5-chloro-2-(2-methylpropoxy) benzyl)-N-ethylamino]pyridazine-3-carboxamide;
N-(3,5-dimethylisoxazol-4-ylsulphonyl)-6-[N-(5-chloro-2-cyclopentyloxy)benzyl)-N-ethylamino]pyridazine-3-carboxamide;
N-(trifluoromethylsulfonyl)-6-[N-(5-chloro-2-cyclopentyloxy)benzyl)-N-ethylamino]pyridazine-3-carboxamide;
N-propanesulfonyl-6-[N-(5-chloro-2-cyclobutylmethoxy) benzyl)-N-ethylamino]pyridazine-3-carboxamide;
N-(3,5-dimethylisoxazol-4-ylsulphonyl)-6-[N-(5-chloro-2-cyclobutylmethoxy)benzyl)-N-ethylamino]pyridazine-3-carboxamide;
6-[N-(5-bromo-2-(2-methylpropoxy)benzyl)-N-ethylamino] pyridazine-3-carboxylic acid;
6-[N-(5-chloro-2-(2-methylpropoxy)benzyl)-N-ethylamino] pyridazine-3-carboxylic acid;
6-[N-(5-bromo-2-(cyclopropylmethoxy)benzyl)-N-ethyl] pyridazine-3-carboxamide;
5-[6-(N-[5-bromo-2-(cyclopropylmethoxy)benzyl]-N-ethylamino)pyridazin-3-yl]tetrazole;
5-(6-[N-(5-chloro-2-(2-methylpropoxy)benzyl)-N-ethylamino]pyridazin-3-yl-tetrazole;
N-propanesulphonyl-6-[N-(5-bromo-2-(cyclopropylmethoxy)benzyl)-N-ethylamino]pyridazine-3-carboxamide;
6-[N-(5-bromo-2-(2-hydroxy-3,3,3-trifluoropropoxy) benzyl)-N-ethylamino]pyridazine-3-carboxylic acid;
5-[6-(N-[2-(cyclopropylmethoxy)-5-methanesulphonylbenzyl]-N-ethylamino)pyridazin-3-yl] tetrazole;
5-[6-(N-[5-bromo-2-propoxybenzyl]-N-ethylamino) pyridazin-3-yl]tetrazole;
6-(N-[5-bromo-2-propoxybenzyl]-N-ethylamino) pyridazine-3-carboxylic acid;
N-propyl-6-(N-[5-bromo-2-propoxybenzyl]-N-ethylamino) pyridazine-3-carboxamide;
N-(3,5-dimethylisoxazo-4-ylsulphonyl)-6-(N-[5-bromo-2-propoxybenzyl]-N-ethylamino)pyridazine-3-carboxamide;
6-[N-(5-chloro-2-(cyclopropylmethoxy)benzyl)-N-ethylamino]pyridazine-3-carboxamide;
6-[N-(5-chloro-2-(cyclopropylmethoxy)benzyl)-N-ethylamino]pyridazine-3-carboxylic acid;
5-[6-(N-[5-chloro-2-cyclopropylmethoxybenzyl]-N-ethylamino)pyridazin-3-yl]tetrazole;

N-trifluoromethanesulphonyl-6-[N-(5-chloro-2-cyclopropylmethoxybenzyl)-ethylamino]pyridazine-3-carboxamide;

6-[N-(5-chloro-2-cyclopentoxybenzyl)-N-ethylamine]pyridazine-3-carboxamide;

6-[N-(5-chloro-2-cyclopentoxybenzyl)-N-ethylamine]pyridazine-3-carboxylic acid;

5-[6-(N-[5-chloro-2-cyclopentoxybenzyl]-N-ethylamino)pyridazin-3-yl]tetrazole;

N-(3,5-dimethylisoxazol-4-ylsulphonyl)-6-[N-(5-bromo-2-(2-methylpropoxy)benzyl)-N-ethylamino]pyridazine-3-carboxamide;

6-[N-(5-methanesulphonyl-2-(cyclopropylmethoxy)benzyl)-N-ethylamino]pyridazine-3-carboxylic acid;

N-(propanesulphonyl)-6-[N-(5-methanesulphonyl-2-(cyclopropylmethoxy)benzyl)-N-ethylamino]pyridazine-3-carboxamide;

N-propanesulphonyl-6-[N-(5-bromo-2-(2-methylpropoxy)benzyl)-N-ethylamino]pyridazine-3-carboxamide;

N-(3,5-dimethylisozazol-4-ylsulphonyl)-6-[N-(5-bromo-2-(3,3,3-trifluoro-2-hydroxypropoxy)benzyl)-N-ethylamino]pyridazine-3-carboxamide;

6-[N-(5-bromo-2-(cyclobutyloxy)benzyl)-N-ethylamino]pyridazine-3-carboxylic acid;

5-[6-(N-[5-bromo-2-(3,3,3-trifluoro-2-hydroxypropoxy)benzyl]-N-ethylamino)pyridazin-3-yl]tetrazole;

6-[N-(5-chloro-2-cyclobutylmethoxybenzyl)-N-ethylamino]pyridazine-3-carboxylic acid;

6-[N-(5-bromo-2-cyclopropylmethoxybenzyl)-N-propylamine]pyridazine-3-carboxylic acid;

N-(3,5-dimethylisoxazol-4-ylsulphonyl)-6-[N-(5-bromo-2-cyclopropylmethoxybenzyl)-N-propylamine]pyridazine-3-carboxamide;

6-[N-(5-bromo-2-cyclopropylmethoxybenzyl)-N-methylamino]pyridazine-3-carboxylic acid;

N-(3,5-dimethylisoxazol-4-ylsulphonyl)-6-[N-(5-bromo-2-cyclopropylmethoxybenzyl)-N-methylamino]pyridazine-3-carboxamide; or a pharmaceutically-acceptable salt of any foregoing compound.

14. A method of relieving pain in a patient suffering therefrom, said method comprising administering to said patient an effective amount of a compound of claim 1.

* * * * *